US007514222B2

(12) United States Patent
Baltzer

(10) Patent No.: US 7,514,222 B2
(45) Date of Patent: Apr. 7, 2009

(54) SITE SELECTIVE ACYLATION

(75) Inventor: Lars Baltzer, Göteborg (SE)

(73) Assignee: Modpro AB, Göteborg (SE)

( * ) Notice: Subject to any disclaimer, the term of this patent is extended or adjusted under 35 U.S.C. 154(b) by 450 days.

(21) Appl. No.: 10/495,512

(22) PCT Filed: Nov. 18, 2002

(86) PCT No.: PCT/SE02/02091

§ 371 (c)(1), (2), (4) Date: May 14, 2004

(87) PCT Pub. No.: WO03/044042

PCT Pub. Date: May 30, 2003

(65) Prior Publication Data

US 2006/0234291 A1    Oct. 19, 2006

(30) Foreign Application Priority Data

Nov. 21, 2001  (SE)  ..................... 0103898
Aug. 19, 2002  (SE)  ..................... 0202473

(51) Int. Cl.
*G01N 33/53* (2006.01)
*C12P 21/06* (2006.01)
*C12N 15/00* (2006.01)
*C12N 5/00* (2006.01)
*C12N 5/02* (2006.01)
*C07H 21/04* (2006.01)
*A61K 38/00* (2006.01)

(52) U.S. Cl. ...................... 435/7.1; 435/68.1; 435/69.1; 435/320.1; 435/325; 514/12

(58) Field of Classification Search .................. None
See application file for complete search history.

(56) References Cited

U.S. PATENT DOCUMENTS

| 6,171,189 | B1 * | 1/2001 | Katano et al. ................. 463/43 |
| 2004/0053241 | A1 * | 3/2004 | Baltzer .......................... 435/6 |
| 2004/0161815 | A1 * | 8/2004 | Baltzer ....................... 435/68.1 |
| 2006/0165712 | A1 * | 7/2006 | Baltzer .................... 424/185.1 |
| 2006/0234291 | A1 * | 10/2006 | Baltzer ........................ 435/7.1 |

FOREIGN PATENT DOCUMENTS

WO   WO 98/55501   12/1998
WO   WO 01/85756   5/2001

OTHER PUBLICATIONS

Linda K. Andersson et al., "*Multifunctional Folded Polypeptides From Peptide Synthesis and Site-Selective Self-Functionalization—Practical Scaffolds in Aqueous Solution*", ChemBioChem 2002, vol. 3, pp. 741 to 751.
Linda K. Andersson et al., "*Control of Lysine Reactivity in Four-Helix Bundle Proteins by Site-Selective $pK_a$ Depression: Expanding the Versatility of Proteins by Postsynthetic Functionalisation*", Chem. Eur. J. 2002, vol. 8, No. 16, pp. 3687 to 3697.
Klas Broo et al., "*Site Selectivity in Self-Catalysed Functionalization of Helical Polypeptide Structures*", J. Chem. Soc., Perkin Trans. 2, 1997, pp. 397 to 398.
Linda K. Andersson et al., "*The Effect of Glycosylation on the Structure of Designed Four-Helix Bundle Motifs*", The Royal Society of Chemistry, 2000, J. Chem. Soc., Perkin Trans. 2, pp. 459 to 464.
Lars Baltzer et al., "*Designed Four-Helix Bundle Catalysts—The Engineering of Reactive Sites for Hydrolysis and Transesterification Reactions of p-Nitrophenyl Esters*", Bioorganic & Medicinal Chemisty vol. 7, (1999), pp. 83-91.
Lars Baltzer et al., "*De Novo Design of Proteins—What are the Rules?*", Chem. Rev. 2001, vol. 101, pp. 3153 to 3163.

* cited by examiner

*Primary Examiner*—Cecilia Tsang
*Assistant Examiner*—Marcela M Cordero Garcia
(74) *Attorney, Agent, or Firm*—Buchanan Ingersoll & Rooney PC

(57) ABSTRACT

Disclosed are novel polypeptides of a four helix bundle formed of two dimerized helix-loop-helix motifs, wherein either both have a sequence according to SEQ. ID No. 1, SEQ. ID No. 2, SEQ. ID No. 3, SEQ. ID No. 4, SEQ. ID No. 5, or SEQ. ID No. 7, or one has a sequence according to SEQ. ID No. 6, and the other one has a sequence according to SEQ. ID No. 1, SEQ. ID No. 2, SEQ. ID No. 3, SEQ. ID No. 4, SEQ. ID No. 5 or SEQ. ID No. 7. Also disclosed is a method for site-selective acylation of a folded polypeptide or protein based on the use of a four helix bundle formed of two dimerized helix-loop-helix motifs folded in an antiparallel mode, said helix-loop-helix motifs comprising amino acid residues in a heptad repeat pattern (a b c d e f g)$_n$, wherein all but 1-3 of said amino acid residues in positions a and d are non-polar and wherein said 1-3 amino acid residues in positions a and d that are non-polar, are selected from the group consisting of lysine, ornithine, diaminobutyric acid and homolysine, wherein said amino acid residues in positions a and d form a hydrophobic core, wherein the polypeptide and/or protein to be acylated is placed in an aqueous solution and an acylation agent is added.

2 Claims, 17 Drawing Sheets

```
            1                            10             15              19
       Ac-N-A-A-D-Nle-E-A-A-I-K-A-L-A-E-K-Nle-A-A-K
                                                            20     23
                                                           -G-P-V-D
                     40              34 33                            24
       NH₂CO-G-A-R-A-F-A-E-F-Orn-K-A-L-Q-E-A-Nle-Q-A-A
```

| Peptide | 10 | 12 | 13 | 15 | 19 | 33 | 34 |
|---------|----|----|----|----|----|----|----|
| KA-I | K | L | A | K | K | K | Orn |
| KA-I-A₁₅ | K | L | A | A | K | K | Orn |
| KA-I-A₃₃ | K | L | A | K | K | A | Orn |
| KA-I-R₁₉ | K | L | A | K | R | K | Orn |
| KA-II | K | K | L | K | R | K | A |

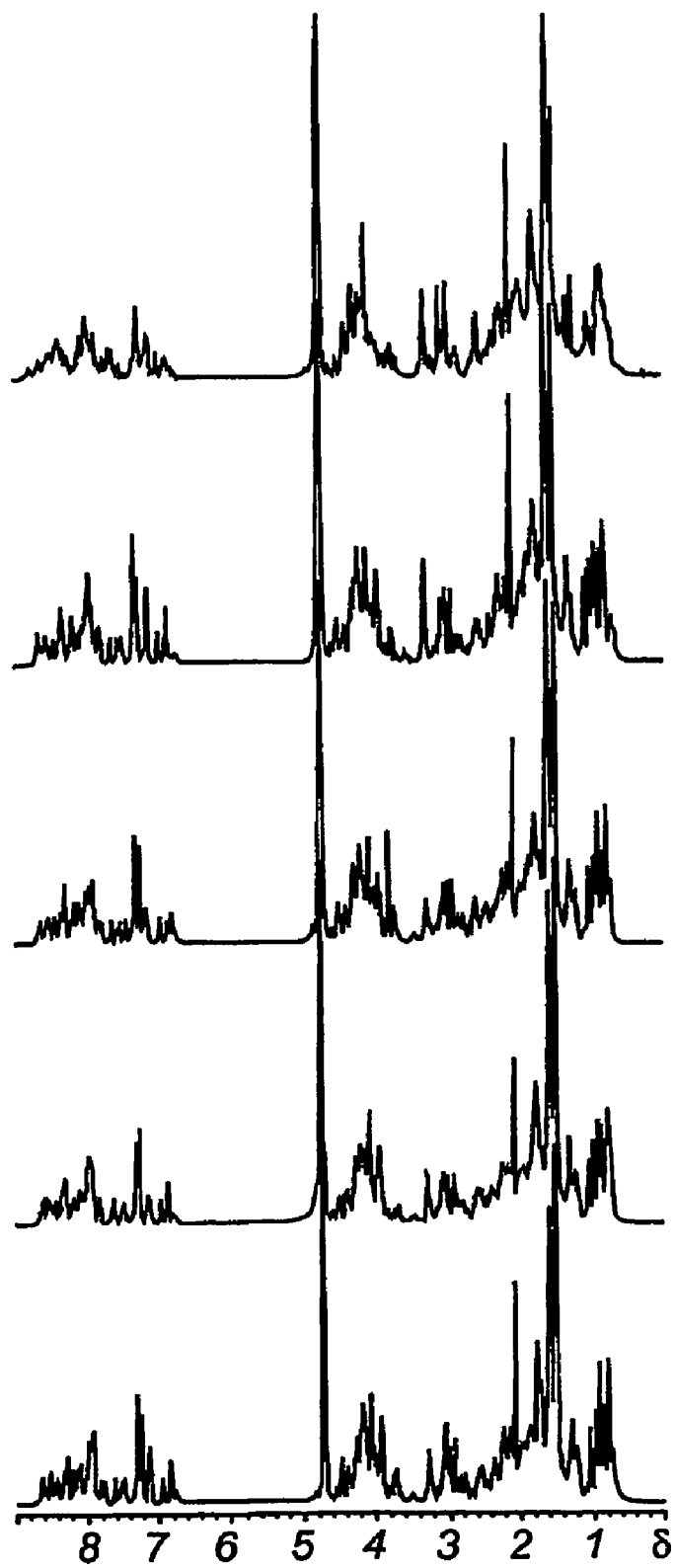

1

```
          1                            11       15         19
NH2-N-A-A-D-Nle-E-A-A-I-K-H-L-A-E-K-Nle-A-A-K
                                      20    23
                                      -G-P-V-D
    42                 34                           24
HOOC-G-A-R-A-F-A-E-F-Orn-K-A-L-Q-E-A-Nle-Q-A-A
```

*Scheme 1*
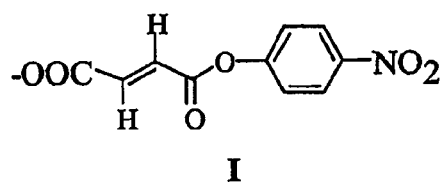
I
*Scheme 2*
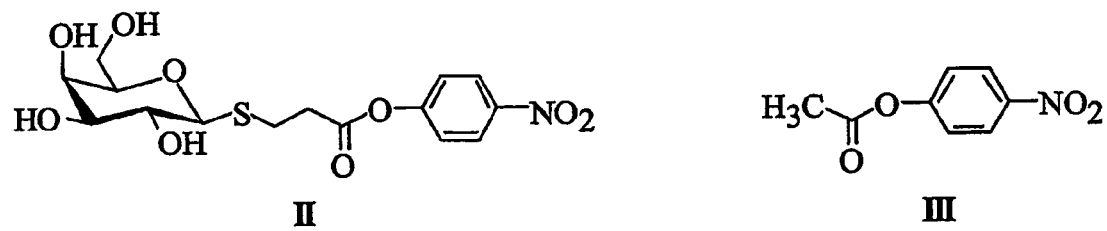
II     III
*Scheme 3*
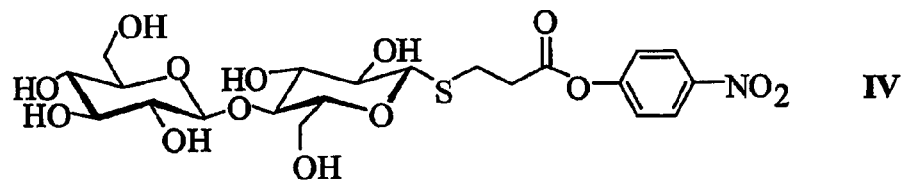
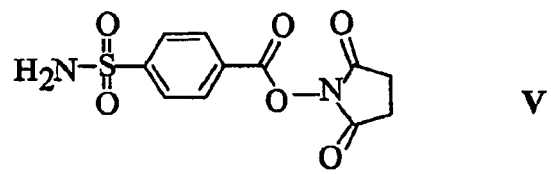
V
*Fig. 17*

*Supporting information. Medium-range NOEs typical of α-helix formation, αH-NH (i, i+1), (i, i+2), (i, i+3) and (i, i+4) fund in LA-42h*

SITE SELECTIVE ACYLATION

FIELD OF THE INVENTION

The present invention relates to the novel polypeptides and to a method for site selective acylation.

BACKGROUND OF THE INVENTION

The versatility of proteins makes it possible for complex cellular functions to proceed smoothly, reliably and at a level of efficiency much envied by chemists. A vast array of chemical transformations and molecular recognition phenomena play key roles in the life processes and tremendous opportunities are now becoming apparent in employing the sophisticated protein scaffold and machinery for tailor-made purposes. Designed enzymes, ligands and receptors as well as molecular devices can be envisioned to have a wide spectrum of applications in chemistry, biomedicine and biotechnology.

The functional richness of proteins, based on artificial as well as the naturally occurring amino acids, is now beginning to be explored in designed proteins for purposes of catalysis and binding [W. F. DeGrado, C. M. Summa, *Annu. Rev. Biochem.* 1999, 68, 779-819; L. Baltzer, *Curr. Opin. Struct. Biol* 1998, 8, 466-470; C. Micklatcher, J. Chmielewski, *Curr. Opin. Chem. Biol.* 1999, 3, 724-729; L. Baltzer, J. Nilsson, *Curr. Opin. Biotechnol.* 2001, 12, 355-360]. The magnitude of the available binding energy that arises from charge-charge, hydrogen bonding and hydrophobic interactions in aqueous solution [A. Fersht, W. H. Freeman and Company, New York, 1999] as well as the capacity of polypeptides for forming a wide range of well-defined tertiary structures make proteins unrivalled molecular scaffolds for probing and exploiting molecular recognition and interactions.

Functional diversity beyond that of folded linear sequences is created in native proteins by enzyme-mediated posttranslational modifications, where site-specific phosphorylations [D. J. Sweatt, *Curr. Biol.* 2001, 11, R:391-R:394; T. Hunter, *Cell* 2000, 100, 113-127] and glycosylations [R. A. Dwek, *Chem. Rev.* 1996, 96, 683-720; H. Lis, N. Sharon, *Eur. J. Biochem.* 1993, 218, 1-27] are key events in signal transduction, energy storage, immune responses and protein folding. The understanding of how to functionalize folded proteins by controlled reactions would enhance also the repertoire of designed proteins but chemical methods for site-selective functionalization of folded proteins have significant limitations. Substituted thiols can be incorporated if there are Cys residue in the sequence, but if there is more than one cysteine residue the sites of incorporation are statistically controlled and site selectivity is not achieved. Lack of site selectivity characterizes all methods for protein labeling in classical protein chemistry [A. Fersht, W. H. Freeman and Company, New York, 1999] Chemoselective targeting of artificial amino acids [D. S. Kemp, R. I. Carey, *Tetrahedron Letters* 1991, 32, 2845-2848; P. E. Dawson, S. B. Kent, *J. Am. Chem. Soc.* 1993, 7263-7266; G. Tuchscherer, *Tetrahedron Lett.* 1993, 34, 8419-8422; P. E. Dawson, T. W. Muir, I. Clark-Lewis, S. B. H. Kent, *Science* 1994, 776-779] is an attractive approach particularly in combination with recent advances in protein synthesis through chemical ligation [P. E. Dawson, T. W. Muir, I. Clark-Lewis, S. B. H. Kent, *Science* 1994, 776-779; J. P. Tam, Y. Lu, C. Liu, J. Shao, *PNAS* 1995, 92, 12485-12489]. Template assisted synthesis of proteins (TASP) combines chemoselectivity and orthogonal protection group strategies with the concept of a peptide scaffold for the formation of designed topologies and self-assembled protein structures [M. Mutter, S. Vuileumier, *Angew. Chem. Int. Ed. Engl.* 1989, 28, 535-554].

Chemical approaches for the site-selective functionalization of folded proteins based on the reactivities of the naturally occurring amino acids are attractive as they provide opportunities for using the powerful methods of molecular biology for selection and screening. Lessons learnt from the modification of model proteins are likely to be of use in functionalizing biologically relevant proteins that cannot be synthesized. Self-catalyzed reactions are very efficient with regards to the incorporation of functional groups and the cost and effort of introducing expensive substituents are considerably less than by synthetic routes, because the amounts needed in the direct reaction with folded proteins are much smaller. The inventor and co-workers have previously reported on a His-Lys mediated site selective functionalization reaction where the side chains of flanking lysine residues in a designed four-helix bundle protein were acylated at pH 5.9 in aqueous solution upon reaction of the peptide with activated esters [L. Baltzer, A.-C. Lundh, K. Broo, S. Olofsson, P. Ahlberg, *J. Chem. Soc., Perkin Trans.* 2 1996, 1671-1676; K. Broo, A.-C. Lundh, P. Ahlberg, L. Baltzer, *J. Am. Chem. Soc.* 1996, 118, 8172-8173; L. Andersson, G. Stenhagen, L. Baltzer, *J. Org. Chem.* 1998, 63, 1366-1367]. In the first, and rate-limiting step of the reaction the unprotonated form of the histidine attacks the ester to form an acyl intermediate. The acyl group is then transferred to the flanking lysine in a fast intramolecular reaction and an amide is formed at the lysine side chain. If several lysine residues are available then at low pH the ones that flank His residues are acylated, whereas those that are far from His residues remain unmodified. If there is more than one lysine in close proximity to the His residue the site of modification is determined by intramolecular competition between the flanking lysines [L. K. Andersson, G. T. Dolphin, J. Kihlberg, L. Baltzer, *J. Chem. Soc., Perkin Trans.* 2 2000, 459-464.

Biomolecular supramolecular chemistry in aqueous solution is the cornerstone of the life processes. The self-assembly of linear peptides into folded proteins is the pathway by which complex structures for catalysis and binding are formed that are capable of discrimination between the components of the vast biological pool of biomacromolecules and metabolites with almost perfect precision. In addition to the complexity that arises from the naturally occurring amino acids and the large number of available folding motifs [C. Branden, J. Tooze, *Introduction to Protein Structure*, Garland Publishing, Inc., New York, 1991, Chapter 2], covalent posttranslational modifications add considerable structural and functional variability [H. Lis, N. Sharon, *Eur. J. Biochem.* 1993, 218, 1-27; R. A. Dwek, *Chem. Rev.* 1996, 96, 683-720; T. Hunter, *Cell* 2000, 100, 113-127; D. J. Sweatt, *Curr. Biol.* 2001, 11, R:391-R:394]. In spite of the opportunities provided by the diversity of protein scaffolds they have, so far, not been explored by chemists for manmade purposes to any significant degree, probably due to the difficulties encountered in understanding protein folding. Recent advances in de novo protein design [J. W. Bryson, S. F. Betz, H. S. Lu, D. J. Suich, H. X. Zhou, K. T. O'Neil, W. F. DeGrado, *Science* 1995, 270, 935-941; C. K. Smith, L. Regan, *Acc. Chem. Res.* 1997, 30, 153-161; B. I. Dahiyat, S. L. Mayo, *Science* 1997, 278, 82-87; C. Micklatcher, J. Chmielewski, *Curr. Opin. Chem. Biol.* 1999, 3, 724-729; L. Baltzer, H. Nilsson, J. Nilsson, *Chem. Rev.* 2001] suggest that new proteins can be designed from scratch and that exciting opportunities are now becoming apparent in chemistry, medicine and biotechnology in designing novel proteins for tailor-made purposes.

The protein scaffold is a versatile building block with well-defined distances and geometries between amino acid residues. In a helical segment the distance between α-carbons is 5.2 and 6.3 Å, if the residues are three or four residues apart in the sequence, respectively, and several residues along the face of a helix can be used to form sites of great complexity. Larger motifs that combine several secondary structure elements increase the number of addressable functional sites as well as the range of interresidue distances. The size and complexity of proteins, even small ones, compare favorably with what is currently achievable in organic compounds designed to self assemble, especially in aqueous solution. Designed proteins therefore have the potential to become practically useful vehicles for a large variety of purposes. The difficulties encountered in understanding the so called protein folding problem should not be underestimated but from de novo design of proteins has emerged an increased understanding of the relationship between sequence and structure. Several de novo designed proteins that fold into native-like structures have been reported, together with their high-resolution NMR structures [B. I. Dahiyat, S. L. Mayo, Science 1997, 278, 82-87; M. D. Struthers, R. P. Cheng, B. Imperiali, Science 1996, 271, 342-345; C. Schafmeister, S. LaPorte, L. J. W. Miercke, R. M. Stroud, Nature Struc. Biol. 1997, 4, 1039; A. J. Maynard, M. S. Searle, Chem. Commun. 1997, 1297-1298; R. B. Hill, W. F. DeGrado, J. Am. Chem. Soc. 1998, 120, 1138-1145; J. W. Bryson, J. R. Desjarlais, T. M. Handel, W. F. DeGrado, Protein Science 1998, 7, 1404-1414; T. Kortemme, M. Ramirez-Alvarado, L. Serrano, Science 1998, 281,253-256], to support the conclusion that we now know how to design proteins that approach and even surpass a hundred residues in size.

Native proteins are posttranslationally modified in enzyme-catalyzed reactions with high efficiency [G. R. Krishna, F. Wold, in Proteins: Analysis and Design (Ed.: R. H. Angeletti), Academic Press, 1998, pp. 121-206], but few chemical reactions exist that provide the precision needed for the site-specific functionalization of manmade proteins. In order for chemists to be able to make full use of designed protein scaffolds chemical reactions are needed that make it possible to address site-selectively several positions for the introduction of multiple functions in controlled geometries. Classical protein chemistry provides many reactions capable of addressing, chemoselectively, specified amino acid residue side chains, but without site selectivity. Chemoselective reactions [D. S. Kemp, R. I. Carey, Tetrahedron Letters 1991, 32, 2845-2848; P. E. Dawson, S. B. Kent, J. Am. Chem. Soc. 1993, 7263-7266; G. Tuchscherer, Tetrahedron Lett. 1993, 34, 8419-8422; P. E. Dawson, T. W. Muir, I. Clark-Lewis, S. B. H. Kent, Science 1994, 776-779] based on the reactivities of functional groups in artificial amino acid residue side chains show great promise, especially in combination with protein synthesis through chemical ligation [P. E. Dawson, T. W. Muir, I. Clark-Lewis, S. B. H. Kent, Science 1994, 776-779; J. P. Tam, Y. Lu, C. Liu, J. Shao, Proc. Natl. Acad. Sci. U.S.A. 1995, 92, 12485-12489]. There are, however, advantages in site-selective functionalization strategies that are based on the exclusive use of the naturally occurring amino acids. The availability of molecular biological methods for selection and screening makes it possible to refine structures and functions and self-catalyzed functionalization reactions based on the reactivities of the naturally occurring amino acids are very economical in terms of the cost of introducing new functions. While the solid-phase peptide synthesis of peptides require that any amino acid derivative to be introduced is added in large excess, typically tenths of moles of material, self-catalyzed reactions are readily carried out in high yields at micromolar amounts.

The inventor and co-workers have previously reported on site-selective functionalization reactions of lysine side chains based on the cooperativity of His-Lys pairs in helical sequences [L. Baltzer, A.-C. Lundh, K. Broo, S. Olofsson, P. Ahlberg, J. Chem. Soc., Perkin Trans. 2 1996, 1671-1676]. The present invention relates to strategies for addressing lysine residues directly in four-helix bundle proteins using activated ester substrates. In the former, His residues react with the ester in a two step reaction [K. Broo, A.-C. Lundh, P. Ahlberg, L. Baltzer, J. Am. Chem. Soc. 1996, 118, 8172-8173]. The first and rate limiting step is the formation of an acyl intermediate at the His side chain under the release of the leaving group. In the second step, the acyl group is transferred in a fast intramolecular reaction to form an amide at the side chain of the Lys residue, even at a pH below 6, where Lys side chains are predominantly protonated. The pKa of a solvent-exposed Lys residue in aqueous solution is 10.4 [C. Tanford, Advan. Protein Chem. 1962, 17, 69-165] and the efficiency of the acylation reaction is ensured by intramolecularity and cooperativity between the His and Lys residues. If the His residue is flanked by more than one Lys, intramolecular competition determines which Lys is acylated [K. Broo, M. Allert, L. Andersson, P. Erlandsson, G. Stenhagen, J. Wigström, P. Ahlberg, L. Baltzer, J. Chem. Soc., Perkin Trans. 2 1997, 397-398]. In a helix the Lys four residues towards the C-terminal (i,i+4) from the position of the His (i) is the preferred site of acylation, in comparison with the position three residues towards the N-terminus (i,i−3).

DESCRIPTION OF THE INVENTION

The present invention relates to a reaction that is based exclusively on the reactivity of the naturally occurring amino acids that will permit the site-selective incorporation of several substituents in a controlled fashion into folded proteins. An understanding of the reactivity of surface exposed amino acids, both in terms of how to control the pKa of ionizable residues and in terms of how to obtain cooperativity between groups of amino acids, made it possible to develop this functionalization strategy.

Unprotonated lysine residues are more efficient nucleophiles than unprotonated His residues [W. P. Jencks, J. Carriuolo, J. Am. Chem. Soc. 1960, 82, 1778-1786] and in order to enhance the repertoire of the four-helix bundle protein scaffold the inventor and co-workers have investigated strategies for controlling lysine pKa values to explore the site-selectivity of the direct acylation of Lys residues. Here the inventor wishes to report on the successful exploitation of the properties of four-helix bundle proteins structurally developed because of hydrophobic interactions between amphiphilic helices. The micro-environment provided by residues designed to form the hydrophobic core was probed with regards to its effect on the ionization constants of lysine residues. The results shed considerable light on the factors responsible for lysine reactivity in surface exposed positions and form the basis for a new strategy for the site-selective functionalization of folded proteins in aqueous solution. According to the basic part of the invention, preferably 1-3 polar amino acid residues in the hydrophobic core of the helix-loop-helix motif are directly acylated.

Another part of the invention relates to efficient and stepwise incorporation of 2-20 different acyl groups per dimerized helix-loop helix motif in a designed, folded four-helix bundle protein scaffold without intermediate steps of purification. It includes but is not limited to the incorporation of three different substituents, which is the example given here. The number of substituents to be incorporated depends on the application at hand and can be two but is only limited by the number of addressable amino acid residues in the folded motif. The acyl groups used here include sugar derivatives, a high-affinity enzyme ligand, an acetyl and a fumaryl residue, but the reactions apply to all active ester substrates. The demonstration for the first time of a strategy for introducing several different substituents into a folded protein, stepwise and site selectively, shows that protein scaffolds are versatile and practically useful building blocks in the design and synthesis of supramolecular compounds for purposes of biomolecular recognition and interaction. Predicted areas of application are biosensors, receptors, catalysts and molecular devices. An especially important aspect of the invention that follows from the fact that the substituents can be introduced without intermediate purification is that the incorporation can be automated and carried out by dispensing robots, for example in the wells of microtiter plates for the purpose of high-throughput applications.

The site selectivity of His mediated lysine and ornithine side chain acylation in a designed four-helix bundle protein scaffold was mapped by reacting several polypeptides with one equivalent of mono-p-nitrophenyl fumarate in aqueous solution at pH 5.9 and room temperature followed by an analysis of the degrees and sites of acylation. Integration of the HPLC chromatograms of the acylated polypeptides and mass spectrometric analysis of the tryptic fragments provided the experimental evidence. Based on these and previously published results a strategy was developed for the site-selective and stepwise incorporation of three residues into a folded polypeptide in aqueous solution at room temperature. However, the invention is by no means limited to the incorporation of three substituents, but is in fact applicable for the incorporation of a single substituent as well as up to twelve substituents per helix-loop-helix monomer. The number of substituents to be incorporated depends on the application and on the number of addressable amino acid residues in the folded scaffold. As an example the incorporation of three substituents will be described. The first substituent was incorporated by reacting a 1.7-fold excess with the polypeptide at pH 5.9, the second substituent was introduced in a 3-fold excess after raising the pH to 8 and the third substituent was incorporated by reacting a 10-fold excess with the polypeptide at pH 5.9. No intermediate steps of purification were taken and the overall yield was 30% or more. Examples of substituents to be included were carbohydrates, an enzyme inhibitor, a fumarate and an acetate group. The introduction of different substituents into three individually addressable positions in a stepwise, efficient and controllable reaction demonstrates that designed folded polypeptides are practically useful scaffolds that are synthesized using very simple chemistry , in aqueous solution. Predicted applications include, designed receptors, biosensors and molecular devices.

Thus, the present invention relates to novel polypeptides consisting of a four helix bundle formed of two dimerized helix-loop-helix motifs, one of said helix-loop-helix motifs having a sequences according to SEQ. ID. No. 1, SEQ. ID. No. 2, SEQ. ID. No. 3, SEQ. ID. No. 4, SEQ. ID. No. 5 or SEQ. ID. No. 7, and the other, independently of the first, having a sequences according to SEQ. ID. No. 1, SEQ. ID. No. 2, SEQ. ID. No. 3, SEQ. ID. No. 4, SEQ. ID. No. 5 or SEQ. ID. No. 7.

The present invention also relates to novel polypeptides consisting of a four helix bundle formed of two dimerized helix-loop-helix motifs, one of said helix-loop-helix motifs having a sequences according to SEQ. ID. No. 6, and the other having a sequences according to SEQ. ID. No. 1, SEQ. ID. No. 2, SEQ. ID. No. 3, SEQ. ID. No. 4, SEQ. ID. No. 5 or SEQ. ID. No. 7.

The invention also relates to a method for site-selective acylation of a folded polypeptide and/or protein based on the use of a chemical structure element consisting of a four helix bundle formed of two dimerized helix-loop-helix motifs folded in an antiparallel mode, said helix-loop-helix motifs comprising amino acid residues in a heptad repeat pattern (a b c d e f g)$_n$. In said heptad repeat pattern (a b c d e f g)$_n$, the amino acids in positions a and d are almost exclusively non-polar, and thereby form a hydrophobic core. However, not all amino acids in positions a and d are non-polar. 1-3 of the amino acid residues in positions a and d are instead polar. Since almost exclusively amino acids in positions a and d are non-polar, this replacement of 1-3 of them with polar amino acid residues does not disturb the formation of the hydrophobic core. Said 1-3 polar amino acid residues in positions a and d are, independently of each other, selected from polar, nucleophilic amino acid residues containing a primary amino group in the side chain. They are preferably selected from the group consisting of lysine, ornithine, diaminobutyric acid, and homolysine, and most preferably they are lysines. This incorporation of 1-3 polar and nucleophilic amino acid residues in positions a and d, results in an enhanced reactivity towards esters.

According to the method of the present invention, the above described polypeptide and/or protein to be acylated is placed in an aqueous solution. An acylation agent is added to the aqueous solution, if such an acylating agent is not already present in the solution, resulting in site-selective acylation of one of said 1-3 polar and nucleophilic amino acid residues in positions a and d.

Preferably, the pH the aqueous solution comprising and the acylation agent is adjusted to approximately 8. The invention does not require that the pH is adjusted to 8, because the site selectivity is due to competition between the available nucleophilic residues in the polypeptide scaffold, and that is unaffected by the pH. However, it is more convenient to run the reaction at high pH because it is faster. In the preferred embodiment described further below, when the helix-loop-helix motif comprises a histidine in position i it is necessary to increase the pH to 8, to increase the site selectivity, for the purpose of competing with the His-mediated acylation reaction.

Furthermore, the invention relates to different applications and use of said method.

The characterizing features of the invention will be more evident from the following description and the appended claims.

For use in the method according to the invention the helix-loop-helix motifs preferably comprises 42 amino acid residues, and preferably the nucleophilic amino acid residues are then present in positions 5, 9, 12, 16, 19, 27, 31, 34 and/or 38. As explained above, only a few residues can be polar and nucleophilic in each motif, the majority of the residues must remain non-polar or the dimer will not fold, but any one of the nine different a or d positions may be selected for site-selective functionalization by the introduction of a lysine, ornithine, diaminobutyric acid, homolysine or other nucleophilic residue.

Preferred helix-loop-helix motifs for use according to the invention are those having sequences according to SEQ. ID. No. 1, SEQ. ID. No. 2, SEQ. ID. No. 3, SEQ. ID. No. 4, SEQ. ID. No. 5 or SEQ. ID. No. 7, or alternatively a motif according to SEQ. ID. No. 6, provided it is combined with another motif having a sequence according to SEQ. ID. No. 1, SEQ. ID. No. 2, SEQ. ID. No. 3, SEQ. ID. No. 4, SEQ. ID. No. 5 or SEQ. ID. No. 7.

The above method may be combined with the methods disclosed in WO 97/43302, WO 01/85756 and WO 01/85906. This combination constitutes a preferred embodiment of the invention. According to this preferred embodiment, said chemical structure element comprises at least one histidine in position i. The polar amino acids to be acylated are situated in positions i+4 and/or i−3. "Situated in positions i+4 and/or i−3" mean that the lysine, ornithine, diaminobutyric acid and/or homolysine is placed four amino acid residues upstream the histidine in position i, and/or three amino acid residues downstream the histidine in position i. The location of histidine and lysine, ornithine, diaminobutyric acid or homolysine, respectively, results in that the histidine is spatially close to the lysine, ornithine, diaminobutyric acid or homolysine. The distance i+4 corresponds approximately to 6.3 Å, and the distance i−3 corresponds approximately to 5.2 Å. If several lysines, ornithines, diaminobutyric acids and/or homolysines are present, the one closest to the histidine which provides the lowest transition state energy will be acylated first.

Preferably, each of said helix-loop-helix motifs comprises 42 amino acid residues. The polar amino acid residues are then preferably present in 2-3 of the positions 5, 9, 12, 16, 19, 27, 31, 34 and/or 38. The helix-loop-helix motifs may thus independently of each other have a sequence according to SEQ. ID. No. 1, SEQ. ID. No. 2, SEQ. ID. No. 3, SEQ. ID. No. 4, SEQ. ID. No. 5 or SEQ. ID. No. 7. Furthermore, one of said helix-loop-helix motifs may have a sequences according to SEQ. ID. No. 6, and the other a sequence according to SEQ. ID. No. 1, SEQ. ID. No. 2, SEQ. ID. No. 3, SEQ. ID. No. 4, SEQ. ID. No. 5 or SEQ. ID. No. 7.

According to this preferred embodiment the method for site-selective acylation of a folded polypeptide and/or protein based on the use of a chemical structure element consisting of a four helix bundle formed of two dimerized helix-loop-helix motifs folded in an antiparallel mode, said helix-loop-helix motifs comprising amino acid residues in a heptad repeat pattern (a b c d e f g)$_n$, wherein all but 1-3 of said amino acid residues in positions a and d are non-polar and wherein said 1-3 amino acid residues in positions a and d that are polar independently are selected from the group consisting of lysine, ornithine, diaminobutyric acid and homolysine, wherein said amino acid residues in positions a and d form a hydrophobic core, comprises the following steps:

the polypeptide and/or protein to be acylated is placed in an aqueous solution an acylation agent is added to the aqueous solution, if such an acylation or acylating agent is not already present in the solution;

the pH of the aqueous solution is adjusted to 5-6, resulting in acylation of the polar amino acid in position i+4;

the pH is then optionally adjusted to 8, resulting in an increase of the reactivity of a pK$_a$ lowered amino acid residue in position d in the hydrophobic core, and a second acylation or acylating agent is added, if such an acylating agent is not already present in the solution, resulting in acylation of said polar amino acid in the d position;

if at least one further lysine, ornithine, diaminobutyric acid or homolysine is present, the pH is then optionally adjusted to 5-6, and a third acylation or acylating agent is added, if such an acylating agent is not already present in the solution, resulting in acylation of the polar amino acid in position i−3.

For example, if the histidine is in position 11, and at least one of said helix-loop-helix motifs comprises lysine, ornithine, diaminobutyric acid and/or homolysine in positions 15, 34 and 8, adjustment of the pH of the aqueous solution to 5-6 followed by the addition of an acylating agent, or an acylation agent, will result in acylation of the lysine, ornithine, diaminobutyric acid and/or homolysine in position 15. If this is followed by adjustment of the pH to 8 and addition of a second acylating agent, this will result in acylation of the lysine, ornithine, diaminobutyric acid and/or homolysine in position 34. If this is followed by adjustment of the pH back to 5-6, the addition of the third acylating agent will result in acylation of the lysine, ornithine, diaminobutyric acid and/or homolysine in position 8.

By performing the acylation according to the present invention it is possible to form an amide at the side chain of the amino acid residue which is acylated from the acyl group of any ester and the primary amine of the side chain. Non-limiting examples of such compounds are DNA, PNA, RNA, sugars, peptides, proteins, enzyme inhibitors, components from combinatorial libraries, catalysts, and fluorescent labels.

The method according to the invention can be used for many different applications. Non-limiting examples of these are to mimic naturally occurring components of the immune system, to produce antagonists or agonists for different components of the immune system, to produce functional mimics of antibodies, to produce receptors, such as artificial receptors to be placed on a protein chip for the identification of proteins from a cell lysate or in a solution or for use in separation or purification, to produce multifunctional probes and/or biosensors, to protect proteins from proteolytic degradation, to affect protein folding, to develop vaccines, to incorporate fluorescent groups for identification of proteins and to incorporate paramagnetic relaxation agents for use in magnetic resonance imaging. The invention may e.g. be used in order to avoid non-specific binding to a substrate, such as a biomolecule, e.g. a protein or DNA, a membrane or a cell-surface, in order to enable control of the binding so that only specific binding is obtained. Any further groups that may be acylated may then be used for binding to other, specific substances, for example in order to provide a model protein with specific characteristics. It is especially preferred to use the method for combinatorial production of e.g. receptors, antagonists and agonists, and to produce combinatorial libraries of different compounds.

The invention will now be further explained in the following examples. These examples are only intended to illustrate the invention and should in no way be considered to limit the scope of the invention.

BRIEF DESCRIPTION OF THE DRAWINGS

In the examples, references are made to the accompanying drawings on which:

FIG. 1 also shows the sequences for KA-I, KA-I-

$A_{15}$, KA-I-$A_{33}$, KA-I-$R_{19}$, and KA-II (which also are given in the sequence listing as SEQ. ID. No 2, SEQ. ID. No 3, SEQ. ID. No 4, SEQ. ID. No 5, and SEQ. ID. No 6, respectively).

Figure 2:
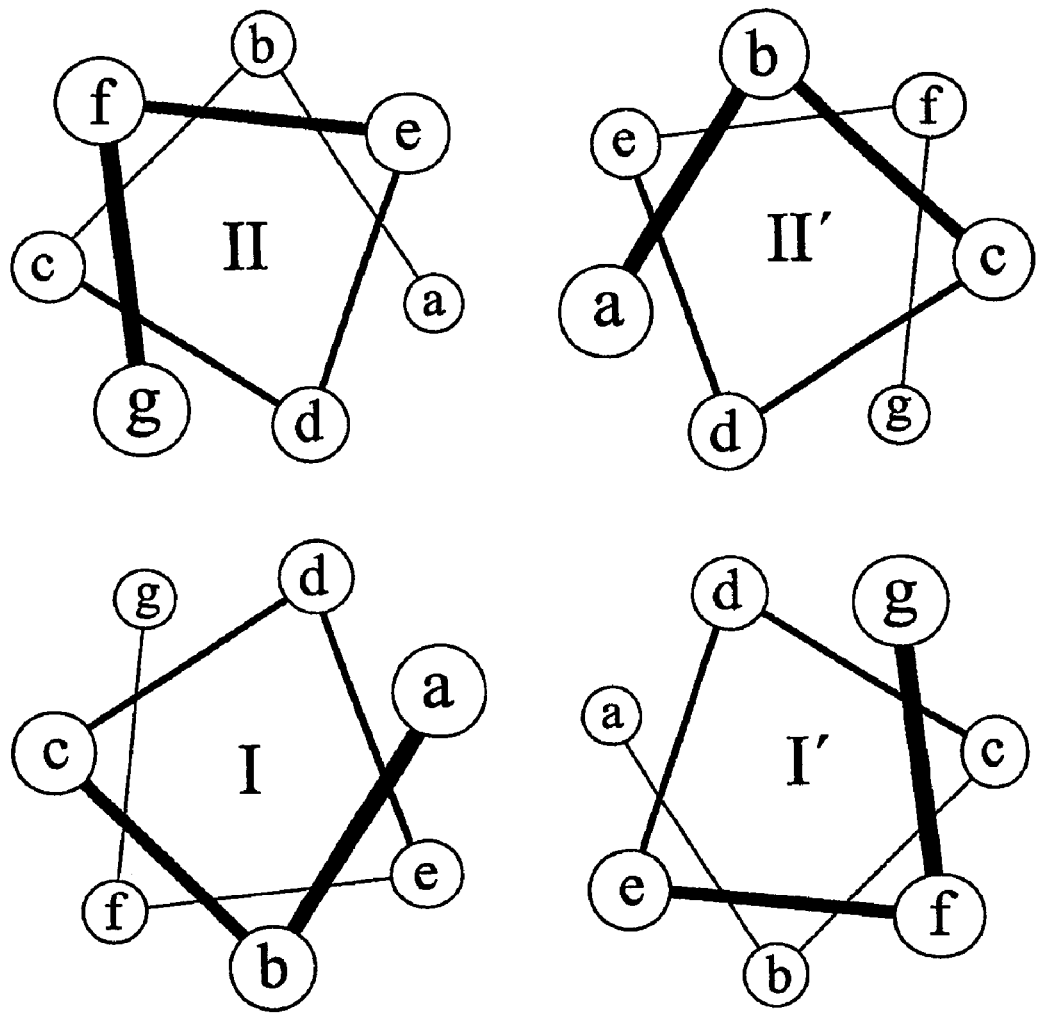

FIG. 2 is a schematic representation of interactions between amphiphilic helices based on the pattern of the heptad repeat. The dimeric structure is folded in an antiparallel mode and the hydrophobic core consists of the residues in a and d positions.

Figure 3:
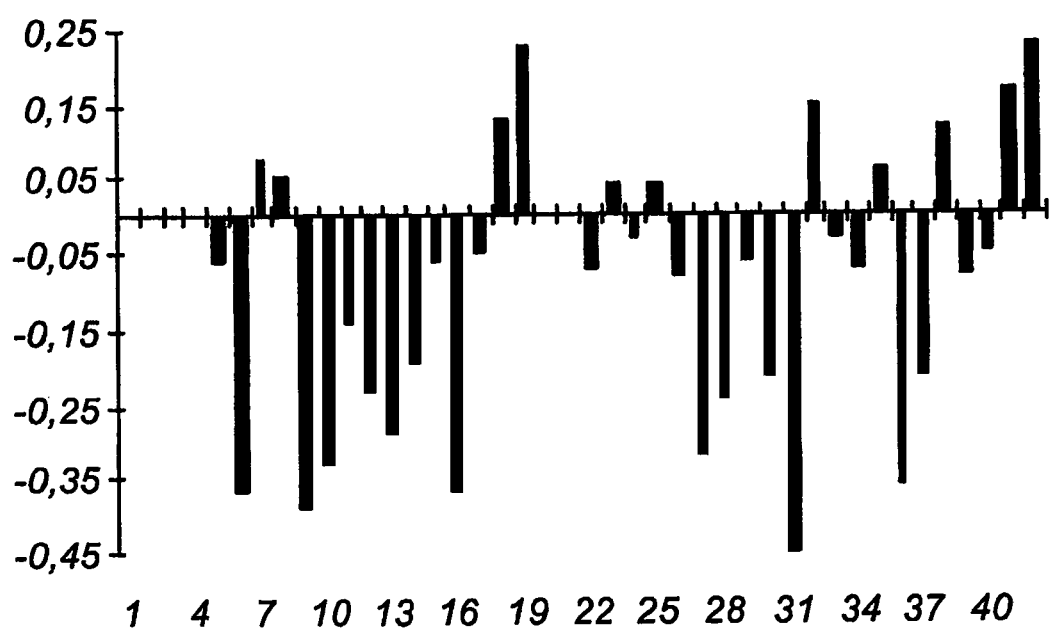

FIG. 3 shows the αH chemical shift deviations from random coil values of the amino acid residues in KA-I. Helical segments are indicated by negative (upfield) shifts and shown between residues 5 and 17, and between residues 26 and 40. The positive, or negligible shifts between residues 18 and 25 suggest a disordered structure and correspond to the residues of the loop region.

Figure 4A:
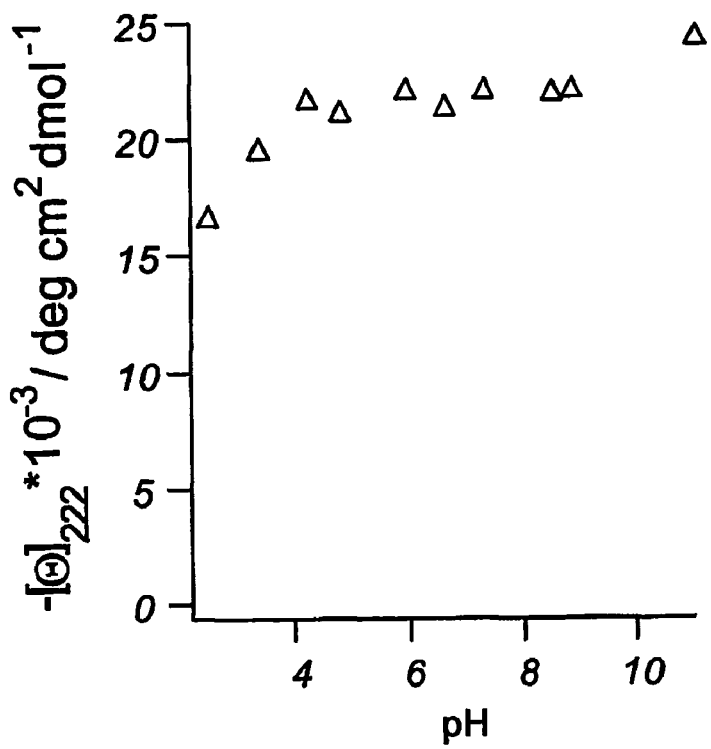
Figure 4B:
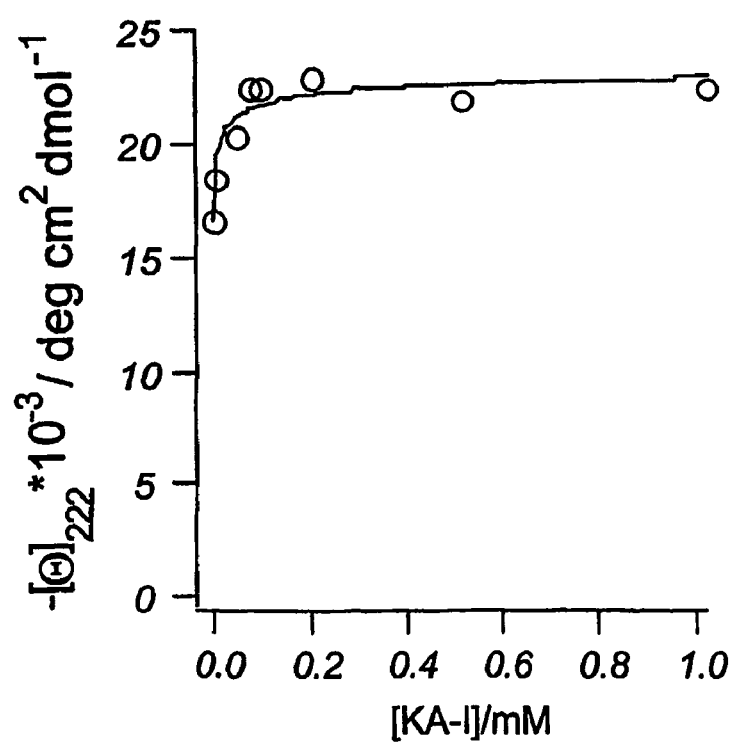

FIG. 4 shows the pH (a) and concentration (b) dependence of the mean residue ellipticity at 222 nm of KA-I. At low pH and low concentration the dimer dissociates to form monomers with low helical contents.

FIG. 5 shows one-dimensional 600 MHz $^1$H NMR spectra of (a) KA-I, (b) KA-I-$A_{15}$, (c) KA-I-$A_{33}$, (d) KA-I-$R_{19}$, (e) KA-II recorded in $H_2O:D_2O$ (90:10 v/v) with 4 vol % TFE-$d_3$ added at 308K and pH 5.2. The chemical shift dispersions and resonance linewidths of spectra a-d are comparable for the series of polypeptides suggesting that in a qualitative sense the folds are not affected to any large extent by the sequence modifications. In KA-II residues in the hydrophobic core have been modified and as a consequence the resonances have become broadened and less dispersed.

Figures 6A, 6B, 6C, 6D:
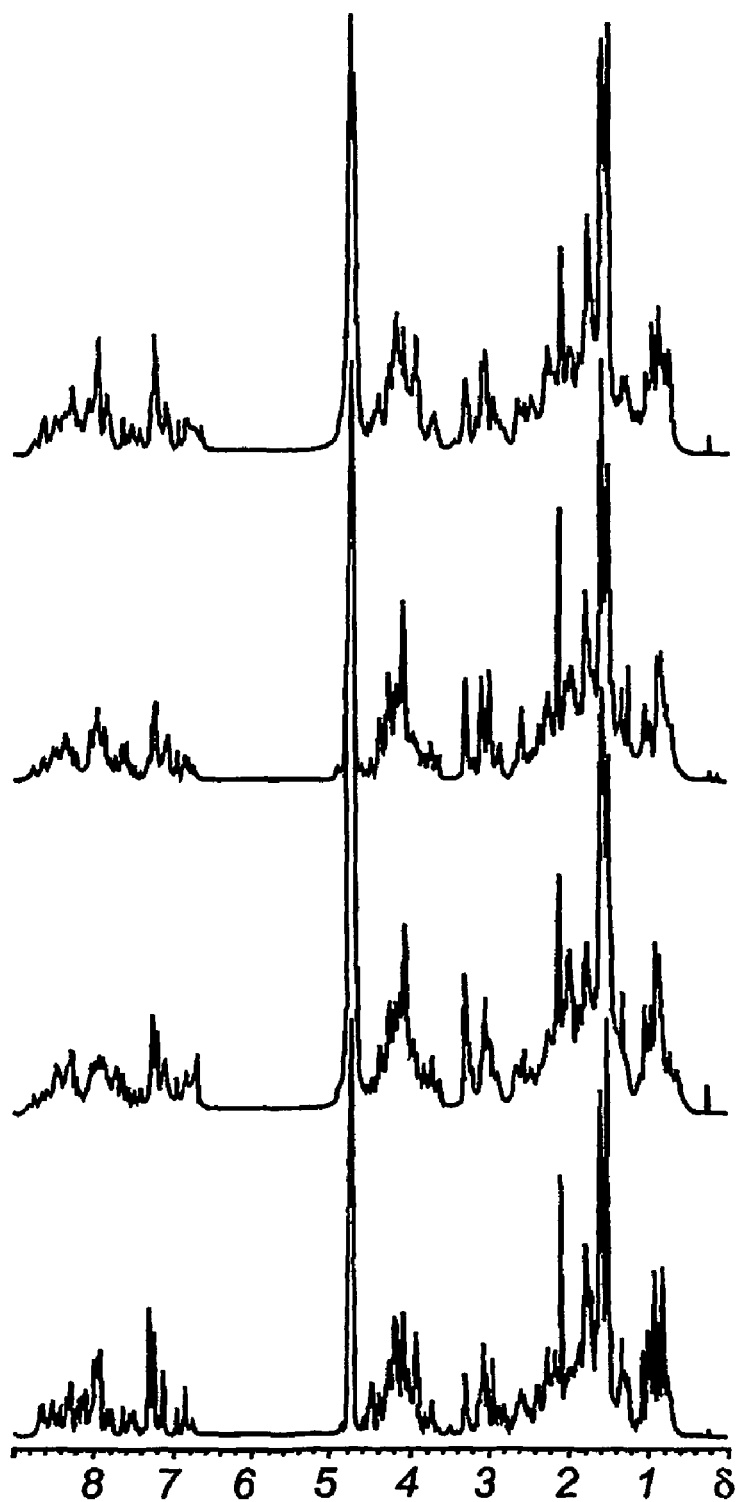

FIG. 6 shows one-dimensional 600 MHz 1H NMR spectra of (a) KA-I, (b) KA-I-Fum, (c) KA-II, (d) KA-II-Fum12 recorded in H2O:D2O (90:10 v/v) with 4 vol % TFE-d3 added at 308K and pH 5.2. The effect of introducing substituents into the folded peptide on the chemical shift dispersion and linewidth is small.

Figure 7:
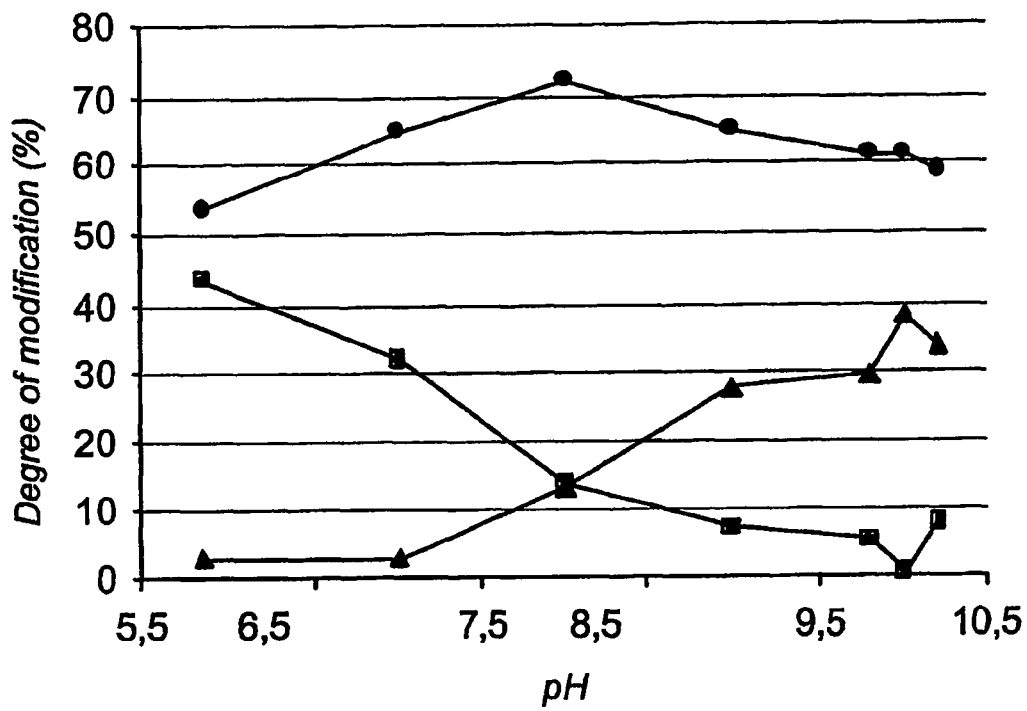

FIG. 7 shows the pH dependence of the degree of modification of KA-I after reaction between KA-I and one equivalent of 1. Unmodified (filled squares), monomodified (filled circles) and dimodified (filled triangles) are observed, after compensation for background hydrolysis.

Figure 8:
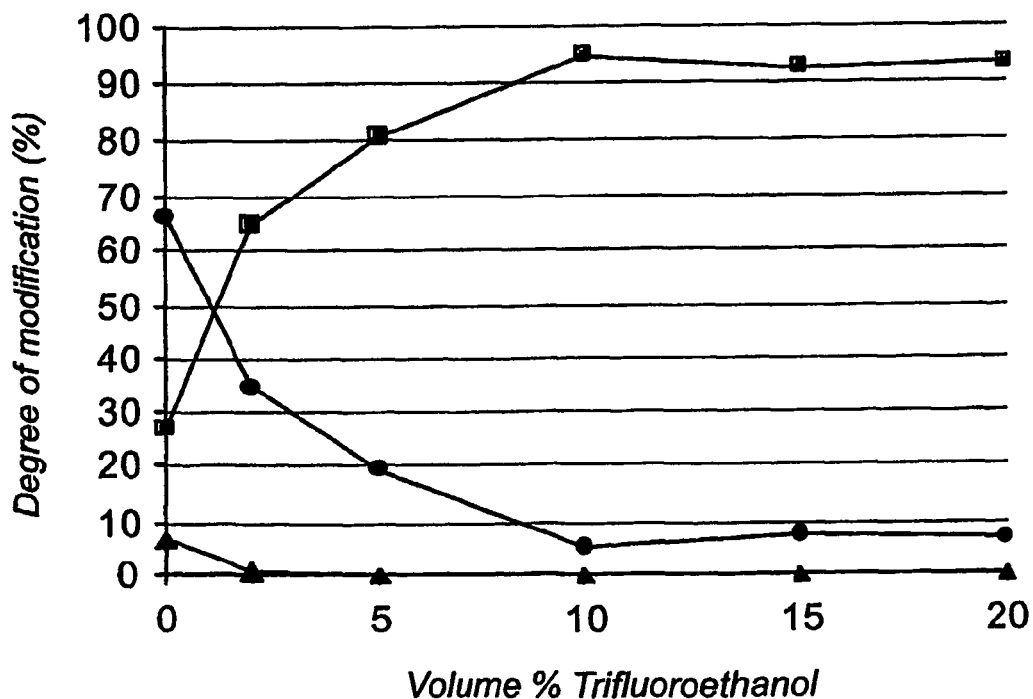

FIG. 8 shows the TFE dependence of the degree of modification of KA-I after reaction between KA-I and one equivalent of 1 at pH 5.9 and room temperature. Unmodified (filled squares), monomodified (filled circles) and dimodified (filled triangles) products were determined.

Figure 9A:
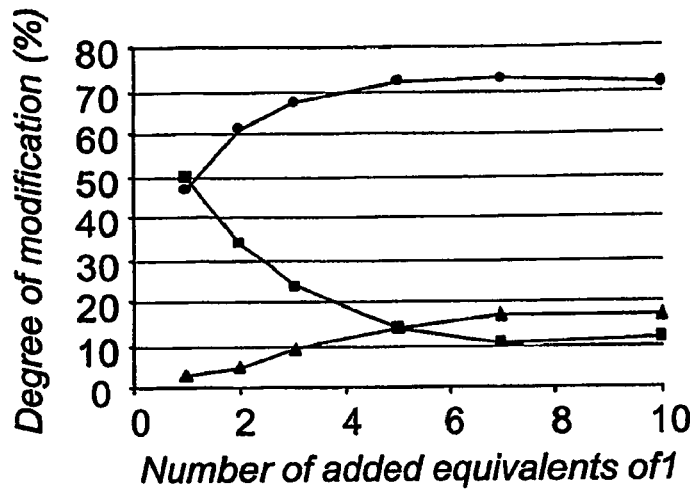
Figure 9B:
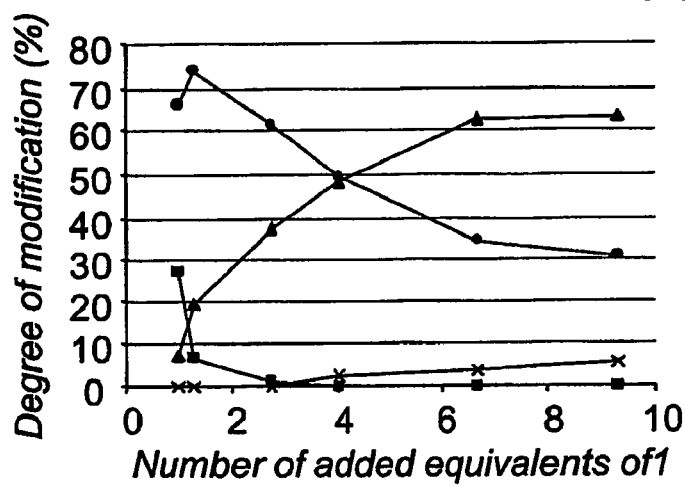
Figure 9C:
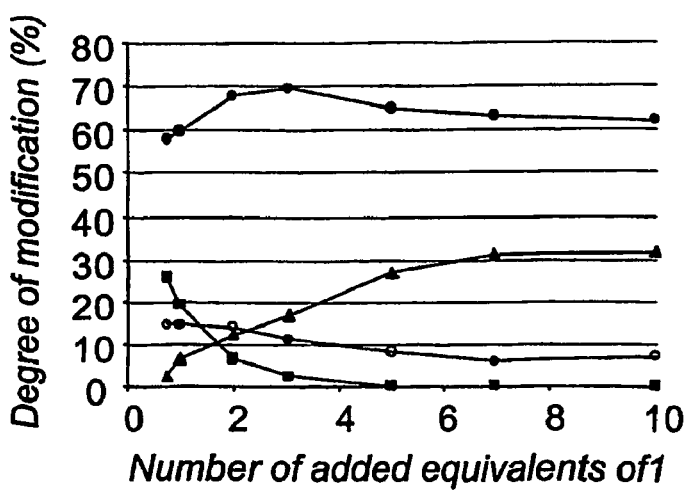

FIG. 9 shows the degree of modification of (a) KA-I at pH 5.9, (b) KA-I at pH 8 and (c) KA-II at pH 8 as a function of the number of added equivalents 1. Unmodified (filled squares), monomodified (filled circles) di-modified (filled triangles) and trimodified products (X) were observed. Filled circles denote the monomodification of Lys12 and open circles denote the monomodification of Lys15.

Figure 10A:
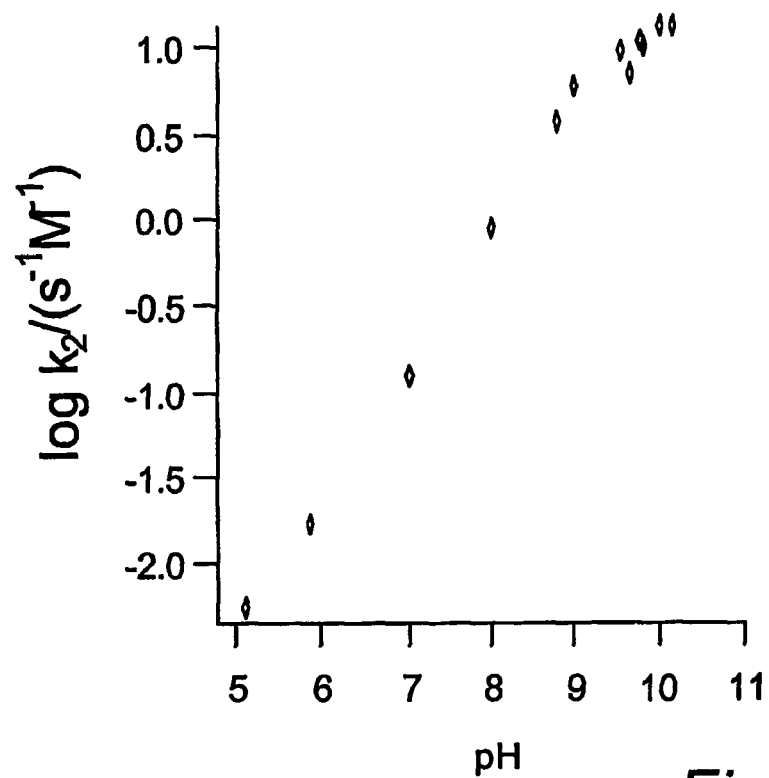
Figure 10B:
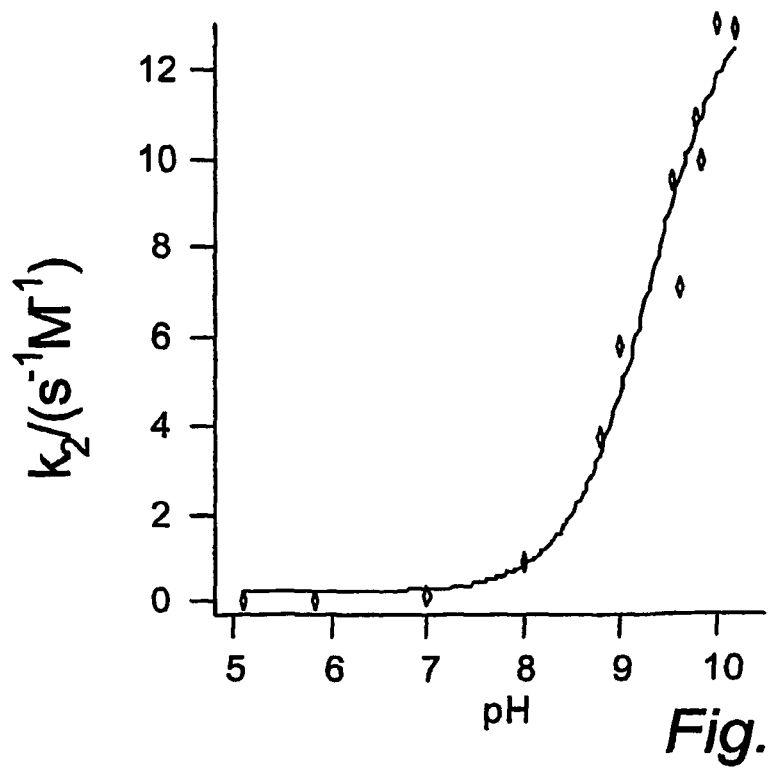

FIG. 10 shows the pH dependence of the logarithm of the second order rate constant (a) and the pH dependence of the second order rate constant (b) for the reaction of p-nitrophenyl fumarate, 1, with KA-I in aqueous solution at 298 K. The solid line in (b) represents an equation describing the dissociation of a monoprotonic acid. The best fit was obtained for a $pK_a$ of 9.3.

Figure 11:
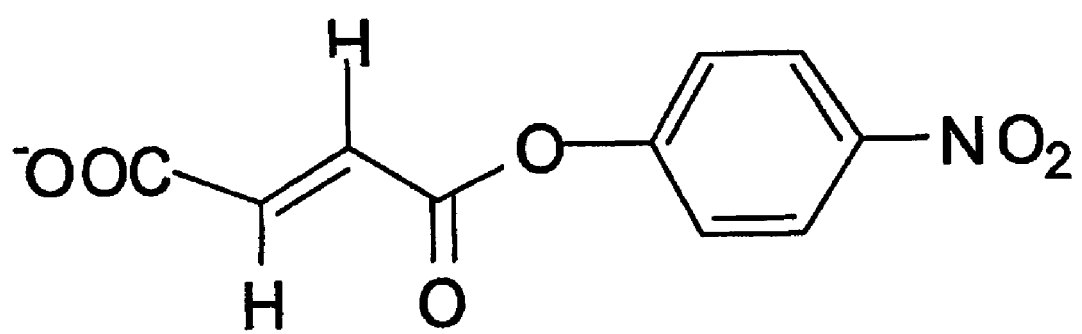

FIG. 11 shows the structure of the substrate fumarate MONOESTER used in the Examples.

Figure 12:
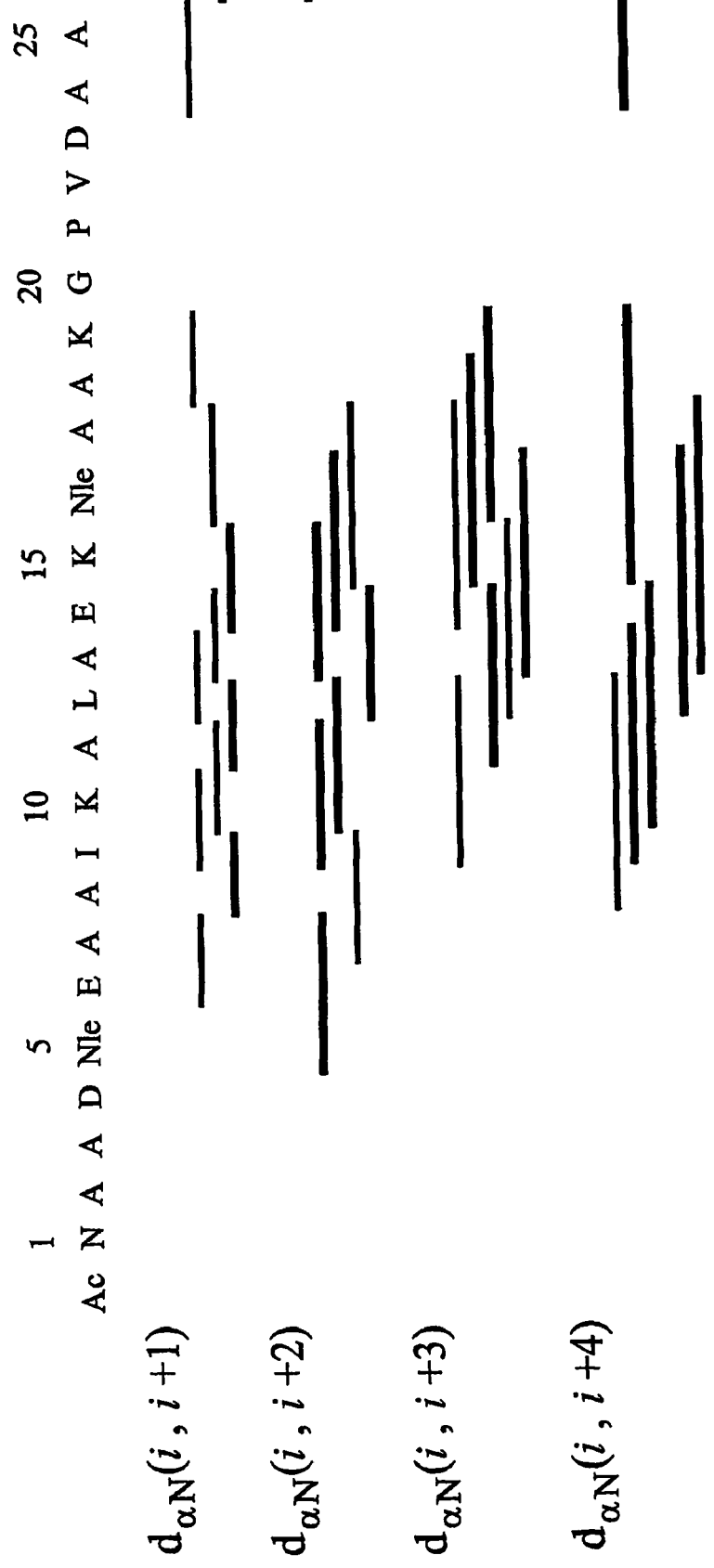

FIG. 12 shows the observed short and medium range NOEs (Nuclear Overhauser Effects) (SEQ ID NO: 8).

Figure 13:
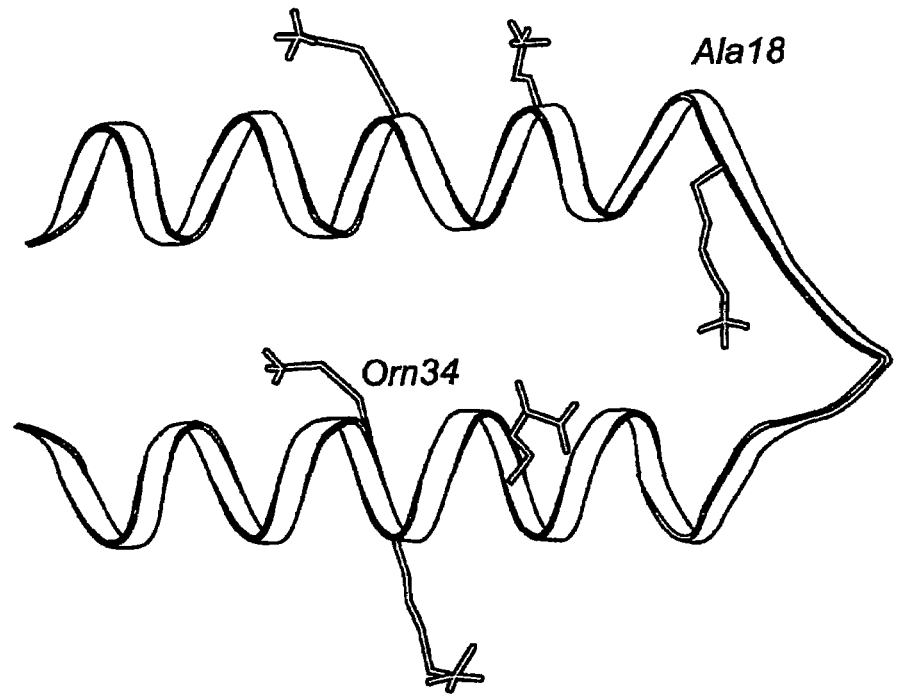

FIG. 13 shows a modeled structure and the amino acid sequence of LA-42b (also given in the sequence listing as SEQ. ID. No. 6) showing the side chains of the residues involved in the acylation reaction. The dimer is the active peptide but for reasons of clarity only the monomer is shown. The one letter code for the amino acids is used, where A is Ala, D is Asp. E is Glu, F is Phe, G is Gly, H is His, I is Ile, K is Lys, L is Leu, N is Asn, P is Pro, Q is Gln, R is Arg, V is Val, Nle is norleucin and Orn is ornithine.

Figure 14:
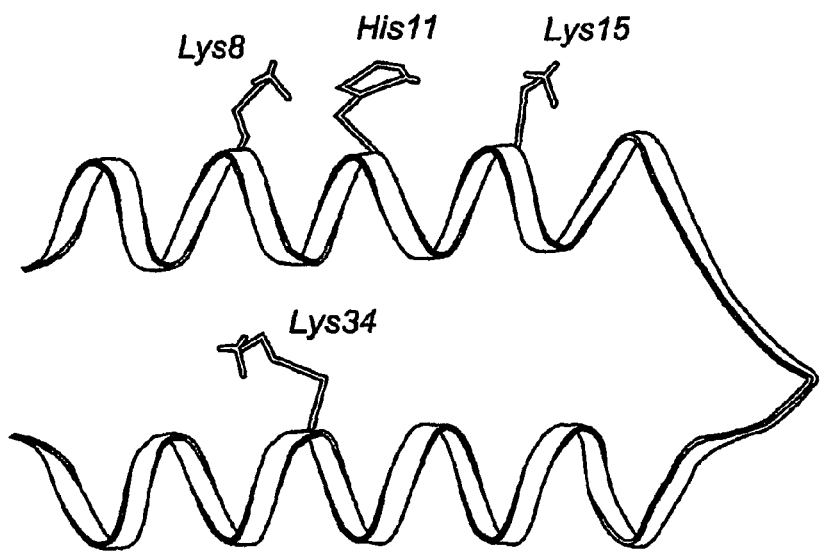

FIG. 14 shows a modeled structure and amino acid sequence of LA-42h (also given in the sequence listing as SEQ. ID. No. 7). The side chains involved in the functionalization are shown. The monomer is shown due to reasons of clarity although the dimer is the active form.

Figure 15A:
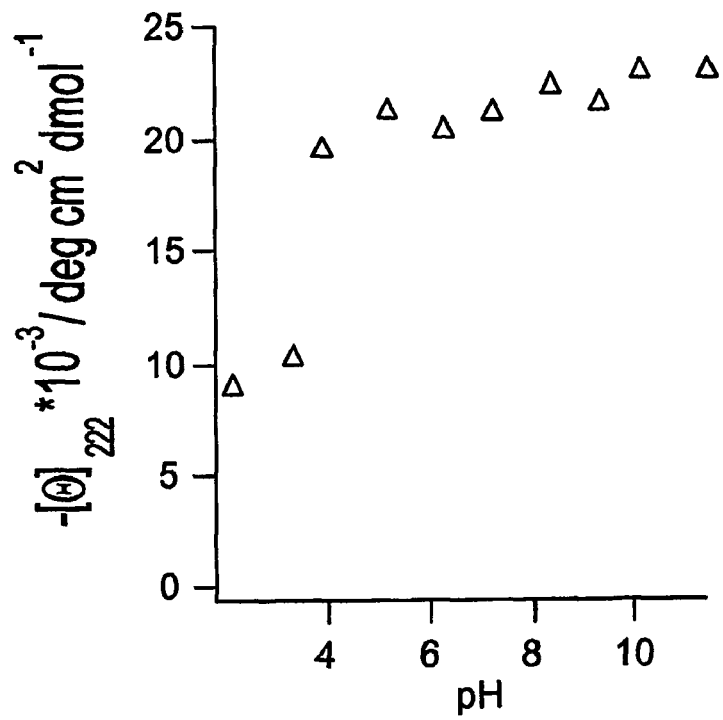
Figure 15B:
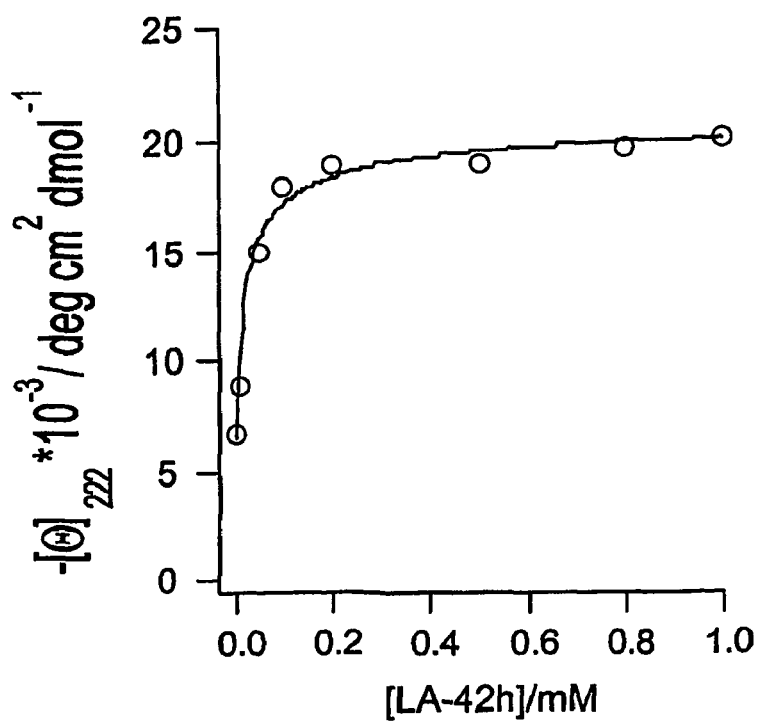

FIG. 15 shows the (a) pH and (b) concentration dependence of the mean residue ellipticity at 222 nm of LA-42h. At a pH below 4 and concentrations below 0.2 mM the dimer dissociates and forms a monomer with low helical content.

Figure 16:
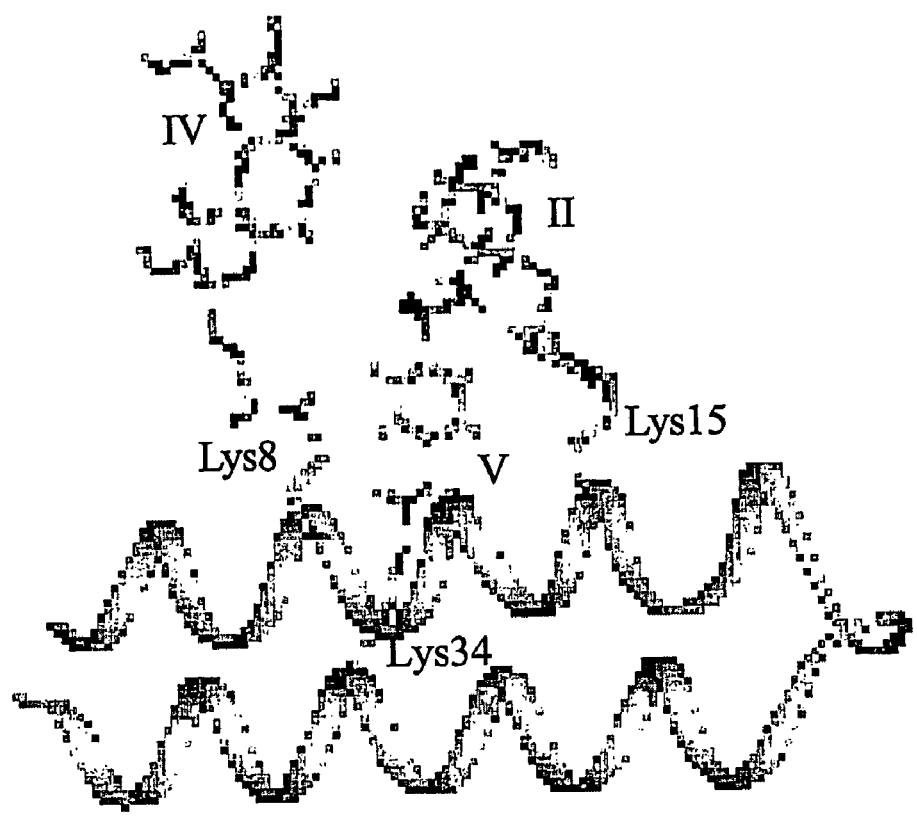

FIG. 16 shows a modeled structure of LA-42h functionalized with galactose, cellobiose and benzenesulfonamide groups.

FIG. 17 shows different esters incorporated according to the Examples.

Figure 18:
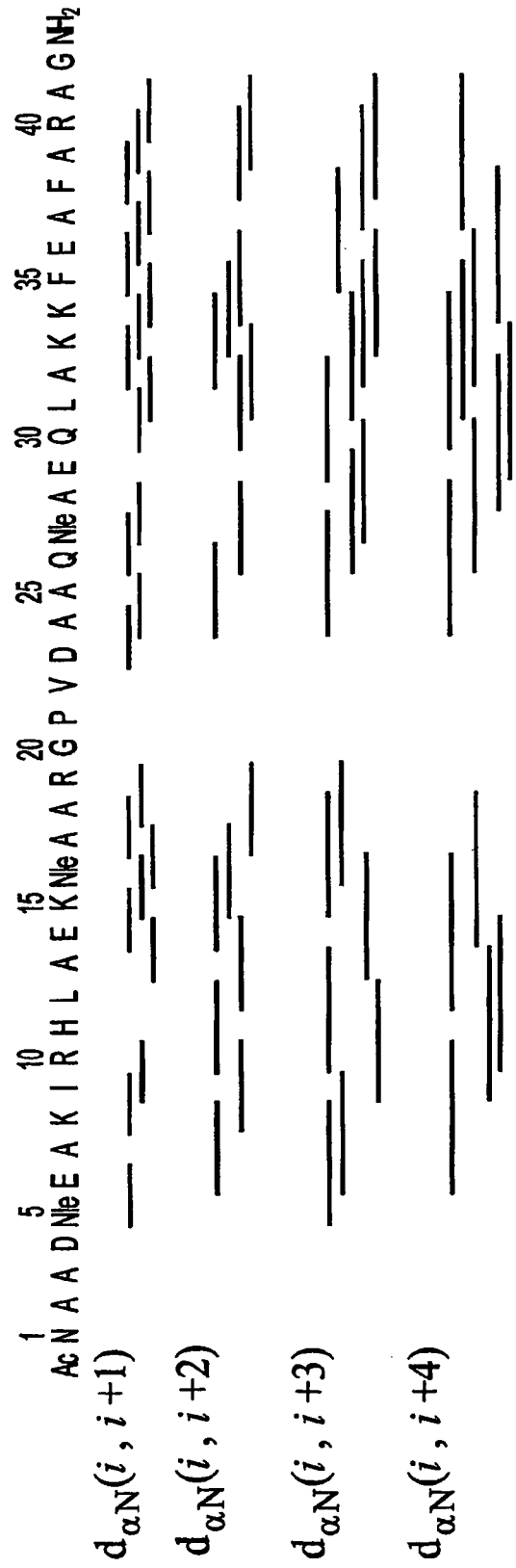

FIG. 18 shows medium-range NOEs typical of α-helix formation, α H—NH (i, i+1), (i, i+2), (i, i+3) and (i, i+4) found in LA-42h (SEQ ID NO: 7).

EXAMPLES

Figure 1:
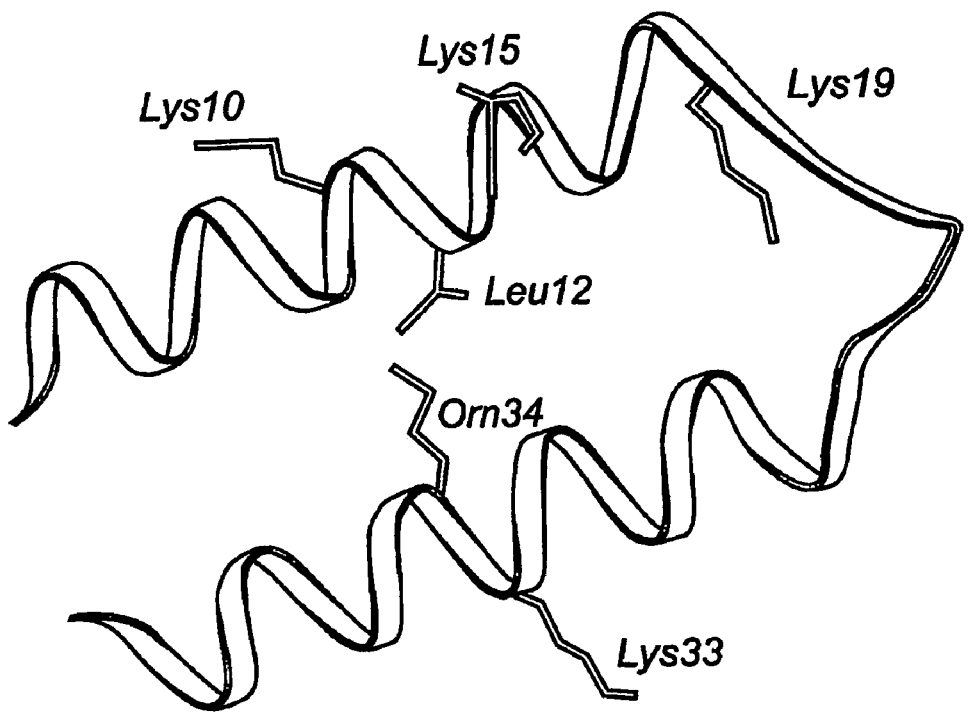
FIG. 1 is a modeled structure and amino acid sequence of KA-I (also given in the sequence listing as SEQ. ID. No 1). The side chains involved in the acylation reaction are shown together with all possible acylation positions. The related peptides have the same sequence as KA-I except for one to three positions where the presented amino acids replace the original. The active peptide is the dimer but for reasons of clarity only the monomer is shown. The one letter code for the amino acids is used, where A is Ala, D is Asp, E is Glu, F is Phe, G is Gly, H is His, I is Ile, K is Lys, L is Leu, N is Asn, P is Pro, Q is Gln, R is Arg, V is Val, Nle is norleucin and Orn is ornithine.

Control of Lysine Reactivity in Four-helix Bundle Proteins by Site-selective pKa Depression Results Design and Structure Five 42-residue sequences have been designed to fold into helix-loop-helix loop motifs and dimerize to form four-helix bundles, FIG. 1. They were synthesized on the solid phase using the Fmoc protection group strategy and an Applied Biosystems Pioneer automated peptide synthesizer. The peptides were purified by reversed-phase (RP) HPLC and identified by MALDI-TOF mass spectrometry (MS) using a Voyager DE-STR mass spectrometer. The design of the peptides reported here was based on those of the peptide sequences SA-42 [S. Olofsson, G. Johanson, L. Baltzer, *J. Chem. Soc., Perkin Trans.* 2 1995, 2047-2056], KO-42 [K. S. Broo, L. Brive, P. Ahlberg, L. Baltzer, *J. Am. Chem. Soc.* 1997, 119, 11362-11372] and LA-42b [L. K. Andersson, G. T. Dolphin, J. Kihlberg, L. Baltzer, *J. Chem. Soc., Perkin Trans.* 2 2000, 459-464] that have been described in detail, previously. In short, these peptides consist of 42 amino acid residues designed to fold in aqueous solution into two amphiphilical helical segments connected by a short loop and dimerize to form four-helix bundles. The amino acid residues of the helical sequences were selected according to their propensity for helix formation and the helices were further stabilized by the introduction of residues capable of interacting with the partial charges of the helix dipole moment, residues capable of salt bridge formation and residues capable of N- and C-terminal capping [J. W. Bryson, S. F. Betz, H. S. Lu, D. J. Suich, H. X. Zhou, K. T. O'Neil, W. F. DeGrado, *Science* 1995, 270, 935-941]. The residues introduced for their structure stabilizing properties were conserved in the design of the polypeptides reported here, FIG. 1, with the minor exception of Lys19 that was replaced by Arg19 in the peptide KA-I-$R_{19}$. The structure formation is mainly driven by hydrophobic interactions between the hydrophobic faces of the amphiphilic helices, the helical content is lost almost completely as the dimers dissociate at low concentration to form monomers [S. Peng Ho, W. F. DeGrado, *J. Am. Chem. Soc.* 1987, 109, 6751-6758].

The design of the four-helix bundle motif is best described in terms of the heptad repeat pattern (a b c d e f g)$_n$, FIG. 2. In an antiparallel four-helix bundle the a and d positions are the nonpolar amino acids that form the hydrophobic core, the g and c positions form the "top" and "bottom" surfaces and the b and e positions are at the interface between the hairpin subunits. Several of the solvent exposed residues in the b, c, e, f and g positions are charged and polar to ensure amphiphilicity and solubility. The a and d residues that make up the hydrophobic cores of SA-42, LA-42b and KO-42 are identical and these residues were also used in the sequences of the peptides reported here, with the exception of KA-II, for reasons explained in detail below. The sequence homology between the sequences KA-I, KA-I-A$_{15}$, KA-I-A$_{33}$ and KA-I-R$_{19}$ and that of LA-42b is more than 95% in each case and the sequence homology between KA-II and LA-42b is more than 88%. Several Lys and one Orn residues were introduced in different positions in order to probe the relationship between site and reactivity and to determine the mechanism of acylation.

The sequence of KA-I is the same as that of LA-42b with the exception that His11 was replaced by Ala11, FIG. 1, to avoid histidine-mediated acylation of lysine residues. In order to determine the hierarchy of reactivities of the Lys and Orn residues of KA-I three peptides were designed in which one Lys was replaced by an Ala or an Arg residue. The sequence KA-I-A$_{15}$ was the same as that of KA-I with the exception that Lys15 was replaced by Ala15. In the sequence KA-I-A$_{33}$ Lys33 was replaced by Ala33 and in the sequence KA-I-R$_{19}$ Lys19 was replaced by Arg19.

To determine whether the enhancement of reactivity observed for Orn34, due to its location in the hydrophobic core d position, was of general applicability, the polypeptide KA-II was designed with an amino acid sequence that was the same as that of KA-I except that Orn34 was replaced by Ala34, Leu12 was replaced by Lys12, Ala13 was replaced by Leu13 and Lys19 was replaced by Arg19. KA-II was designed to probe whether position 12, a d position, would become more reactive than any surface exposed position due to its hydrophobic environment. In order to avoid competition between hydrophobic core positions, Orn34 was replaced by Ala34, to ensure that only one Lys or Orn residue was in an a or a d position.

The structures of SA-42, LA-42b and KO-42 were determined, previously, by NMR and CD spectroscopy [L. K. Andersson, G. T. Dolphin, J. Kihlberg, L. Baltzer, *J. Chem. Soc., Perkin Trans.* 2 2000, 459-464; S. Olofsson, G. Johanson, L. Baltzer, *J. Chem. Soc., Perkin Trans.* 2 1995, 2047-2056; K. S. Broo, L. Brive, P. Ahlberg, L. Baltzer, *J. Am. Chem. Soc.* 1997, 119, 11362-11372; S. Olofsson, L. Baltzer, *Folding & Design* 1996, 347-356] and the states of aggregation of SA-42 and KO-42 were determined by analytical ultracentrifugation. The polypeptides were found to be highly helical and their helical contents were determined from the mean residue ellipticities at 222 nm. The negative deviation of αH-proton chemical shifts from those of random coils, and medium-range NOEs were used to identify helical segments and positive chemical shift deviations were used to identify loop regions. Long-range NOEs were observed that were only compatible with helix-loop-helix hairpin formation and antiparallel hairpin dimerization. The concentration dependences of [θ]$_{222}$ showed that the peptides aggregated to form dimers or higher states of aggregation. In the case of SA-42 and KO-42 the sedimentation equilibrium showed that a dimer was formed with only a slight tendency for further aggregation at close to, and above, mM concentrations. The inventor assume this to be true also for other, similar sequences. High-resolution NMR structures could, however, not be obtained since the hydrophobic cores were disordered and in fast exchange on the NMR timescale. A solid understanding of the structural features of these folded helix-loop-helix dimers was nevertheless obtained and the dominant fold was shown in each case to be in good agreement with the designed structure. In spite of the fact that the peptides in this investigation are highly homologous to the previously designed sequences a determination of the structure of KA-I was undertaken by CD and $^1$H-NMR spectroscopy.

The CD spectrum of KA-I showed the signature characteristic of an α-helical protein with minima at 222 and 208 nm. The mean residue ellipticity at 222 nm was −23900 deg cm2 dmol−1 at pH 5.9 in 50 mM Bis-Tris buffer. The 1H NMR spectrum of KA-I was assigned from the TOCSY and NOESY spectra recorded in H2O:D2O (90:10 v/v) containing 4 vol % of TFE-d3 at 308 K using methods described previously [S. Olofsson, L. Baltzer, *Folding & Design* 1996, 347-356]. Extensive studies of the effect of small amounts of TFE on the NMR spectrum and the solution structure of SA-42 [S. Olofsson, L. Baltzer, *Folding & Design* 1996, 347-356] showed that the NH exchange rates, and the resonance linewidths were reduced, without changing the overall fold of the folded dimer.

The spin systems of most of the amino acids of KA-I (5-22, 24-42) were identified from the TOCSY spectrum. The cis-trans equilibrium of Pro21 in the loop region gives rise to a conformational equilibrium involving some of the flanking residues and a subset of spin systems with low intensity was therefore observed for residues in, and close to, the loop sequence. The sequential assignment was obtained from the NH—NH connectivities determined from the NOESY spectrum. The deviations of the αH chemical shifts from tabulated values of random coil conformations [D. S. Wishart, B. D. Sykes, F. M. Richards, *J. Mol. Biol.* 1991, 222, 311-333] are readily used for identification of secondary structure, and the sequences from Nle5 to Ala17 and from Gln26 to Arg40 were identified as helical regions, FIG. 3. Medium-range NOEs typical of α-helix formation (α H—NH i, i+3 and i, i+4) were found in the sequence from Ala8 to Lys19 in helix I and from Ala24 to Gly42 in helix II, see supporting information. Positive chemical shift deviations, or the absence of deviations from random coil shifts were observed in the sequence from Ala18 to Ala25 which was concluded to form a disordered loop. NOE connectivities between the aromatic protons of the phenylalanine residues and the methyl groups of Ile9, Leu12 and Leu31 showed that the peptide formed a hairpin helix-loop-helix motif. The observation of NOE connectivities between Phe35 and Nle16, and between Nle5 and Lys19, suggested that it dimerized in an antiparallel mode to form the four-helix bundle. This is because NOEs only arise between nuclei separated by less than 5 Å [K. Wüthrich, *NMR of proteins and nucleic acids*, John Wiley & Sons, Inc., 1986] and the distances between Phe35 and Nle16, and between N15 and Lys19, are too long to give rise to NOEs within the monomer and too long to give rise to NOEs in a parallel dimer. The helical content of KA-I was found to be constant in the pH range 4.5-9 and in the concentration range from 0.2-1 mM, FIG. 4*a, b*, under the conditions used for the functionalization reactions. The inventor concludes that KA-I forms an antiparallel dimer of helix-loop-helix hairpin motifs, and that residues in a and d positions are positioned in the hydrophobic core, whereas all other residues are solvent exposed.

The secondary structures of the peptides KA-I-A$_{15}$, KA-I-A$_{33}$, KA-I-R$_{19}$ and KA-II were investigated by CD spectroscopy. The mean residue ellipticities at 222 nm at 1 mM concentrations were in the range from −21000–−25500 deg cm² dmol⁻¹ at pH 5.9 and pH 8, Table 1. Complete NMR spectroscopic analyses were not carried out for these peptides due to the high degree of sequence homologies with KA-I but qualitative evaluations of structures were obtained from their 1D $^1$H NMR spectra, FIG. 5. The $^1$H NMR spectra of native proteins in contrast to those of random coil conformations are characterized by large chemical shift dispersions. For folded polypeptides that are partly disordered the chemical shift dispersion is intermediate between those of native proteins and random coils but resonances are severely broadened in comparison with those of both native proteins and random coils. An inspection of the 1D spectra of closely related sequences therefore provides, a qualitative view of whether substantial structural changes have occurred due to the sequence modification. The 600 MHz NMR spectra of all four polypeptides at 1 mM concentration in 4 vol % TFE-d₃ in $H_2O:D_2O$ (90:10 v/v) at pH 5.2 and 308K offered no indications that the sequence modifications have affected the polypeptide fold. The linewidths and chemical shift dispersions were largely unaffected.

The effects of acylation on the structures of the polypeptides KA-I-Fum and KA-II-Fum$_{12}$ were probed by inspection of their $^1$H-NMR and CD spectra, FIG. 6 and Table 1. The incorporation of fumaryl residues was found not to influence the structures of KA-I and KA-II, significantly, in the qualitative sense described above.

The Acylation Reaction.

The peptides were reacted with mono-p-nitrophenyl fumarate, 1, at room temperature in aqueous solution at pH 5.9 and at pH 8. The reaction mixtures were purified by RP HPLC and the reaction products were shown to be polypeptides amidated by fumaric acid and identified as unmodified, monomodified or dimodified peptides by MALDI-TOF MS. The observed molecular weights corresponded well to the calculated ones. Typically the difference was less than 0.5 mass units, and in no case was it larger than 1.1 mass units. No other modifications were detected but some unreacted starting material remained as the ester 1 was partly consumed by competing background hydrolysis to form fumaric acid and p-nitrophenol. The reactivities of individual lysine residues were monitored by measuring the degree and position of acylation in the reaction between one equivalent of 1 and each of the polypeptides at pH 5.9 and at pH 8 at room temperature, Table 2. The degrees of acylation were estimated by integration of the peaks in the analytical RP HPLC chromatogram and the sites of modification in each peptide were identified by MALDI-TOF MS after tryptic digestion of the modified peptides. The degree of acylation of each position of the polypeptides are presented in Table 2.

At pH 8, 66% of KA-I was monoacylated according to the accurate integration of the HPLC chromatogram, corresponding to 90% of the total amount of acylated peptide since some polypeptide remained unmodified. KA-I was monoacylated at position 34 as well as at position 19, both of which were d positions, but the two monoacylated peptides could not be separated by RP HPLC and their relative amounts had to be roughly estimated from the intensities of the tryptic fragments in the mass spectrum. The fraction of KA-I that was monoacylated at Orn34 provided approximately 75% of the tryptic fragments from monoacylated peptide, and the fraction of KA-I monoacylated at Lys19 provided approximately 25%. While mass spectrometry is not a reliable method for quantitative comparisons the inventor feels confident in claiming that the polypeptide acylated at Orn34 is the dominant monoacylated reaction product. An analogous analysis of the acylation pattern of KA-I-A$_{15}$, suggested that approximately 85% of the monoacylated products were acylated at Orn34, and only 15% were acylated at Lys19, demonstrating a high degree of site selectivity.

The Mechanism of the Acylation Reaction.

The degree of mono- and dimodification of KA-I was studied as a function of pH, FIG. 7. One equivalent of 1 was reacted with KA-I at 8 different pH values in the range from 5.9 to 10.2. The reaction mixtures were analyzed by analytical RP HPLC and the degrees of modification were determined from the resulting peaks after identification by MALDI-TOF MS. Monomodification of either Orn34 or Lys19 dominates but at high pH dimodification of both residues is significant. No other lysines were modified and it appears that the pKa values of Lys19 and Orn34 are significantly lower than those of the competing lysine residues. The degree of modification was also determined in aqueous solution at pH 8 as a function of added trifluoroethanol (TFE), FIG. 8, to probe the role of the folded structure on lysine reactivity. The overall degree of modification was reduced substantially already at low fractions of TFE. The degree of monomodification was reduced by a factor of two at 2 vol % TFE, and to less than one third of the value in aqueous solution at 5 vol % TFE. TFE is known to denature-proteins by strengthening helical sequences and disrupting hydrophobic interactions [M. Buck, *Q. Rev. Biophy.* 1998, 31, 297-355]. It is also expected to decrease the pKa of primary amines through a solvent effect, and to decrease the rate of chemical reactions that go through charged transition states. The decreased incorporation of fumaryl substituents was therefore not attributable to a single factor. Nevertheless, the results are compatible with a model where lysine reactivity is reduced as the tertiary structure of the folded polypeptide is disrupted.

The degrees of mono and dimodification of KA-I and KA-II were also studied as a function of the number of added equivalents of 1. At pH 5.9 and at pH 8 one to ten equivalents of 1 were added to a buffered solution of KA-I and the resulting reaction mixtures were analyzed by RP HPLC, FIG. 9*a, b*. The site selectivity was high at low pH, where more than 70% of monomodification was obtained after addition of 5 equivalents of 1, and the only other modification was the introduction of two fumaryl groups. At pH 8 70% of monomodification was observed after the addition of 1.3 equivalents. At pH 8 one to ten equivalents of 1 were also added to a buffered solution of KA-II and the resulting reaction mixtures were analyzed by RP HPLC, FIG. 9*c*. The selectivity was very high as the fraction of monomodified KA-II approached 70% for the addition of 2-3 equivalents of substrate, showing that Lys12, a d position, in KA-II was the most reactive Lys residue.

The second-order rate constant for the reaction between KA-I and 1 was determined at 308 K as a function of pH from pH 5.1 to 10.2. The plot of the logarithm of the second-order rate constant versus pH shows a linear dependence on pH in the range from 5.1 to slightly less than 9, where the plot levels off and approaches pH independence at pH 10.2, FIG. 10*a*. The pH profile shows that the reaction is dependent on an amino acid in its unprotonated form. A function describing the dissociation of a monoprotonic acid with a p$K_a$ of 9.3 gave the best fit to the experimental results, FIG. 10*b*. The expected p$K_a$ of a lysine side chain in a solvent exposed position is 10.4 [C. Tanford, *Advan. Protein Chem.* 1962, 17, 69-165].

Discussion

The understanding of the reactivity of amino acid residues exposed on protein surfaces is a prerequisite for the engineering of protein scaffolds capable of site selective self-functionalization. The inventor and co-workers have previously reported on factors that control histidine reactivity on the surface of a four-helix bundle scaffold [K. S. Broo, L. Brive, R. S. Sott, L. Baltzer, *Folding & Design* 1998, 3, 303-312] and used His Lys pairs for self functionalization by forming thermodynamically stable amide bonds at the side chains of Lys residues [L. Baltzer, A.-C. Lundh, K. Broo, S. Olofsson, P. Ahlberg, *J. Chem. Soc., Perkin Trans.* 2 1996, 1671-1676; K. Broo, A.-C. Lundh, P. Ahlberg, L. Baltzer, *J. Am. Chem. Soc.* 1996, 118, 8172-8173; L. Andersson, G. Stenhagen, L. Baltzer, *J. Org. Chem.* 1998, 63, 1366-1367]. The possibility of addressing Lys residues directly considerably broadens the scope of protein self-functionalization as more groups can be introduced over a larger protein surface area and because the site selectivity may be enhanced when used in combination with the His mediated acylation reaction. The control of lysine reactivity also has important implications in catalysis as primary amines are directly involved in imine formation and thus in aldol condensations and Michael additions. While the measurements of His reactivity depended on the direct determination of pKa values by NMR methods, the corresponding measurement of lysine dissociation constants is difficult mainly because changes in the observed chemical shifts are not directly related to the state of protonation. At the high pH necessary to significantly deprotonate a Lys side chain the structure of the folded polypeptide also changes due to the loss of stabilizing charge-charge interactions between protonated Lys residues and negatively charged aspartate and glutamates, and possibly also due to the drastic change in overall charge. For this reason chemical shift changes are not due only to dissociation but also to changes in structure. The investigation of lysine reactivity is therefore based on the determination of lysine acylation, in reactions between the folded polypeptides and active esters that lead to irreversible amide bond formations at the lysine side chains, readily detectable by mass spectrometry. In addition to the increased understanding of protein reactivity that is expected from the identification of the principles that control lysine acylation, the reactions reported here provide an efficient strategy for the site-selective functionalization of the folded four-helix bundle protein in aqueous solution. It provides the opportunity to introduce multiple substituents stepwise into the folded protein without any need for protection groups or artificial amino acids.

The quantification of reactivity at a pH that is lower than the pKa of the reactive residue requires that the Bronsted coefficient $\beta$ is known. The state of protonation of a basic residue depends on the relationship between the pH and the pKa according to the Henderson-Hasselbach equation, and the relationship between reactivity and pKa follows the Bronsted equation, where the coefficient $\beta$ is unique for each reaction. The coefficient $\beta\beta$ for the reaction between primary amines and p-nitrophenyl acetate is 0.8 [W. P. Jencks, J. Carriuolo, *J. Am. Chem. Soc.* 1960, 82, 1778-1786] and at a pH lower than the pKa values of the Lys and Orn residues the one with the lowest pKa will therefore be the most efficient nucleophile. Because the reaction product in the direct reaction between a primary amine and an ester is an amide, the reaction is irreversible and the degree of acylation in a competition experiment is a direct measure of the difference in reactivity between the competing residues. At pH values above those of the pKa the relative reactivities will be reversed since the primary amines with the highest pKa values will be the most efficient nucleophiles, but protein chemistry at such high pH has little practical use.

The sequence KA-I contains four lysine and one ornithine residues and the structure of the folded polypeptide was determined by NMR and CD spectroscopy. It folds into a helix-loop-helix motif that dimerizes to form a four-helix bundle and the residues can be considered to follow the pattern of the heptad repeat. The experimental system was designed to provide a comparison between the reactivities of several different lysine positions and four modified sequences, FIG. 1, where lysines were replaced by alanine or arginine residues, were synthesized for comparison of their reactivities with that of KA-I. Their structures were studied to a lesser extent than that of KA-I, but the results from a qualitative NMR and CD spectroscopic analysis, and the fact that they are highly homologous to the sequence of KA-I, support the assumption that they, too, form four-helix bundles. In terms of the heptad repeat pattern, FIG. 2, Lys10 is in a b position, Lys 15 is in a g position and Lys33 is in a c position, all positions exposed to the solvent. Lys19 is formally in a d position although it was initially incorporated as a cap for the C-terminus of helix I [S. Olofsson, G. Johanson, L. Baltzer, *J. Chem. Soc., Perkin Trans.* 2 1995, 2047-2056]. The chemical shift deviation of the $\alpha$H of Lys19, FIG. 3, suggests that it is not in a helical conformation but in a more disordered loop. The observation of fingerprint NOE connectivities between Lys19 and Lys15, and between Lys19 and Nle16, see supporting information, however, supports the conclusion that is in fact in a helical conformation, at least part of the time. Lys19 therefore has to be considered to be in a d position. In these peptides Orn was used in position 34, a d position, for comparison with LA42b, which also contains an Orn residue in position 34. The reactivity of Orn is the same as that of Lys as they are both primary amines. The only difference between them is the number of methylene groups in the side chain, and the conclusions about Orn reactivity also apply to that of Lys. In the peptide KA-II Orn34 was replaced by an Ala and Leu12 was replaced by a Lys residue, in order to probe whether position 12 would make a lysine more reactive because of the hydrophobic microenvironment The peptides were reacted at room temperature with one equivalent of mono-p-nitrophenyl fumarate, 1, in aqueous solution at pH 5.9 and at pH 8 so that the Lys and Orn residues were forced to compete for the substrate. Acylation was observed in all cases, but only at two positions in each protein and only at the side chains of lysine or ornithine residues in positions 34, 19 and 15, in the polypeptides KA-I (34 and 19), KA-I-A$_{15}$ (34 and 19), KA-I-A$_{33}$ (34 and 15) and KA-R-$_{19}$ (34 and 15). In KA-II, the dominant position of acylation was position 12 but Lys15 was also modified. Lys10 and Lys33 were not modified in any sequence and there is therefore a difference in reactivity between individual Lys and Orn residues depending on structure. Orn34 is preferentially acylated in all peptides, with the obvious exception of KA-II, and position 34 is therefore the most reactive one. Orn34 is in a d position, and therefore in the hydrophobic core, suggesting that it has a depressed pKa due to the low dielectric constant of the a and d positions. The pH dependence of the acylation of KA-I was determined, FIG. 7, and monoacylation was the only detectable reaction product at pH levels below 8, whereas at higher pH several lysines were acylated simultaneously. Two monoacylated products were obtained, one where Orn34 was selectively acylated and one where Lys19 was acylated, in a very approximate ratio of 3 to 1. According to the $\alpha$H chemical shifts Lys19 is not located in a well-defined helical structure, although measured medium range NOEs suggest that it is, at least part of the time. It is formally in a d position and may have the properties of a partly hydrophobic environment although the influence of Lys15 may contribute to the pKa depression through an electrostatic effect, in analogy to effects observed in His pKa values [K. S. Broo, L. Brive, R. S. Sott, L. Baltzer, *Folding & Design* 1998, 3, 303-312]. Selectively depressed pKa values are compatible with the observed pH dependence and it is suggested that pKa values of Lys residues may be depressed by introducing them into a and d positions to increase their reactivities towards carbonyl groups and other electrophiles.

The second-order rate constant was determined as a function of pH in order to determine the pKa of the reactive residues, FIG. 10. The best fit to the experimental results corresponded to a pKa of 9.3, which amounts to a pKa depression of 1.1 pKa units in comparison with a solvent exposed lysine residue. The reaction was also carried out in TFE to determine the effect on reactivity of disrupting the tertiary structure while retaining a helical conformation, FIG. 8. The overall degree of acylation was dramatically reduced in spite of the fact that lysine pKa values would be expected to decrease due to the lower polarity of the medium. The observed loss in incorporation efficiency is complex and may not be explained in a simple way, but the results are in agreement with a model where the reactivity is reduced when the tertiary structure, which is responsible for the pKa depression, is disrupted. Enhanced reactivities of Lys and Orn residues in a and d positions in comparison with those of residues in other positions are therefore established. Any reaction that depends on the availability of unprotonated Lys residues is therefore a target that can be addressed using this strategy. The fact that no a position has been probed is mainly due to practical considerations. There is no difference in the hydrophobic character between an a or a d position and the same considerations apply.

In order to provide a critical test for whether position 34, a d position, was more reactive because of pKa depression due to the hydrophobic environment, a helix-loop-helix motif was designed where an alanine residue was incorporated into position 34, and a second d position was selected for lysine incorporation. In KA-II Leu12 was replaced by Lys12, and Lys12 was preferentially acylated by 1. Consequently, a and d positions provide environments that are sufficiently hydrophobic to reduce the pKa value of lysine residues and make the incorporation of acyl groups site selective. The incorporation of lysine residues in positions that according to the heptad repeat pattern are hydrophobic is therefore a viable design strategy for site-selective functionalization of folded proteins. Comparable positions in native proteins should be able to provide sites that can be functionalized in a similar way.

In KA-I the selectivity between Orn-34 and Lys19 was probed but it was not possible to separate the monoacylated peptides KA-I-Fum$_{19}$ from KA-I-Fum$_{34}$ by analytical RP HPLC. An analysis of the tryptic digests by MALDI-TOF MS suggests, very approximately, that the level of acylation was 46-51% at position 34 was and 15-20% at position 19, after reaction at pH 8. The preference for Orn34 over that of Lys19 is therefore approximately a factor of 3 at pH 8. These numbers are clearly approximate but there is little doubt that Orn34 is the most reactive position. Lys19 is, however, more reactive towards 1 than all other lysines, no other functionalized peptide was detected. Lys19 is also in a d position in the heptad repeat of amino acids and may also be partly included in the hydrophobic core, although its position in close proximity to the more flexible loop region of the peptide suggests that the pK$_a$ might not be affected as much as that of Orn34. Its position as a C-cap would be expected to raise its pKa due to the interaction with the helix dipole moment, and make it less reactive. The reason may instead be that Lys15 depresses its pKa because of the charge repulsion between the protonated forms of the lysine residues. The role of Lys15 is not understood in detail but substituting an alanine for Lys15 considerably improved the selectivity in favor of Orn34, approximately 85% of all incorporated fumaryl substituents were introduced at the side chain of Orn34 in the sequence KA-I-A$_{15}$. This is in good agreement with a model where Lys15 reduces the pKa of Lys19, and when Lys15 is replaced by Ala the pKa of Lys19 is increased and the reactivity is decreased, leading to enhanced selectivity of Orn34 over Lys19.

Understanding the molecular basis for the reactivity of Lys and Orn residues made it possible to improve selectivity by rational design. Replacing Lys19 by an Arg residue, as in KA-I-R$_{19}$, enhanced the selectivity in favor of Orn34 acylation to a level where 85% of the incorporated fumaryl substituents were introduced at Orn34 to form a monoacylated polypeptide. In the absence of Lys19, Lys15 became the second most efficient nucleophile but it was monoacylated only to a small degree. Possibly Arg19 reduced the pKa of Lys15 to make it more reactive. A more complex relationship was unraveled in the interplay between Lys33 and Lys19. As Lys33 was replaced by Ala Lys19 was no longer reactive enough to compete with Lys15 for the substrate. No acylation of Lys19 was observed and it may be that subtle structural effects play a role although the CD spectrum is largely unaffected by the change in sequence.

The pH dependence of the reaction between KA-I and 1 showed that the reaction depends on the unprotonated form of a residue with a pKa of approximately 9.3, suggesting lysine or ornithine residues. Amide formation is an irreversible reaction under the reaction conditions and the fact that acyl groups were found exclusively at the side chains of Orn34 and Lys19 therefore provided strong evidence in favor of direct acylation of the side chain primary amines. The pH dependence is in principle compatible with a model where flanking Lys and Orn residues carry out general-base catalysis in the formation of the amide bond, but this reaction mechanism is unlikely due to the small fraction of unprotonated lysines and ornithines that is available at low pH. The inventor concludes that Lys and Orn residues are acylated in a one-step reaction and that the reactivity is determined mainly by the position in the sequence where a and d positions provide enhanced reactivity enough to make Lys and Orn residues dominant sites for the incorporation of acyl groups. In addition, close proximity of flanking charged residues appear to affect the pKa of Lys and Orn residues in an analogous manner to what was previously described for His residues [K. S. Broo, L. Brive, R. S. Sott, L. Baltzer, *Folding & Design* 1998, 3, 303-312].

The addition of only one equivalent of 1 makes competitive measurements of acylation more readily interpretable but it leaves some polypeptide unreacted due to competition from background hydrolysis. In order to optimize selectivity KA-I was reacted with up to 10 equivalents of 1 and the degree of acylation and the site selectivity were analyzed, FIG. 9*a*, *b*. The maximum level, 70%, of monoacylated protein was obtained after approximately 5 equivalents were reacted at pH 5.9 and 1.3 equivalents at pH 8. The ratio of monoacylated to diacylated protein was then approximately 72/13 at pH 5.9 and 73/19 at pH 8. Since acylation times are dramatically shorter at the higher pH for practical purposes a high pH is preferable in protein functionalization. Furthermore, the selectivity does not depend on pH as long as it is less than the value of the pKa of the reactive residues as discussed above. In KA-II Lys12 was acylated very efficiently by three equivalents of ester.

Conclusions

The reactivity of Lys and Orn residues may be controlled to a level where they become the dominant nucleophiles of the protein scaffold in reactions with active esters to form functionalized side chains. The underlying principles are therefore of fundamental interest in understanding protein reactivity but also of practical use in developing covalently modified four-helix bundle model proteins with applications as artificial receptors, biosensors and in glycobiology. It was possible after determining the relationship between structure and reactivity to design a polypeptide KA-I-R19 where 85% of site-selectively monoacylated product was obtained and readily purified. It may be possible to design even more selective sites as our understanding of the chemistry of protein surfaces develops. As vehicles for site-selective acylation four-helix bundle proteins have thus been shown to be versatile and useful scaffolds.

Understanding the reactivity of lysine side chains also provides a strategy for designing sites capable of imine formation, the key reaction step in aldol reactions and Michael additions. The main factor in pKa control is the position in the structure of the folded four-helix bundle motif, where their incorporation into a or d positions of the heptad repeat provides a molecular environment capable of depressing the pKa value by 1.1 units in comparison with those of solvent exposed residues. This corresponds to an increase in reactivity by an order of magnitude in the unprotonated state, which is sufficient to ensure a high degree of selectivity in the incorporation of new functionality into folded proteins.

EXPERIMENTAL

General Procedure for MALDI-TOF MS Analysis.

The mass spectra were recorded on an Applied Biosystems Voyager DE-STR MALDI-TOF mass spectrometer. Peptide solutions were prepared at concentrations of approximately 1 mg/mL in 0.1% (v/v) trifluoroacetic acid (TFA). A solution of 10 mg of α-cyano-4-hydroxycinnamic acid in 1 mL of 50% acetonitrile in 0.1% TFA was used as matrix. Typically 2 µl of the peptide solution was mixed with 18 µl of the matrix, and 1 µl of the mixture was applied to the plate for crystallization. A mixture of angiotensin I, ACTH clip1-17, ACTH clip 18-39, ACTH clip 7-38 and insulin (bovine) was used for calibration. Measured molecular weights corresponded to the calculated ones within 1.1 mass units in all cases, and typically within 0.5 mass units.

CD Spectroscopy.

CD spectra were recorded on a Jasco J-715 CD spectropolarimeter, routinely calibrated with d-(+)-10-camphorsulphonic acid, in 0.1, 0.5, 1 or 5 mm cuvettes in the interval from 280-190 nm. Each spectrum is an average of six scans and the background was subtracted from the spectrum before the mean residue ellipticity at 222 nm was measured. For the concentration dependent studies a 50 mM stock peptide solution in BIS-Tris buffer at pH 5.85 was prepared and diluted to the desired concentrations by pipetting. For pH dependence measurements a 0.3 mM aqueous stock solution was prepared and the pH was adjusted by small additions of 0.1 or 1M HCl or NaOH.

NMR Spectroscopy.

NMR spectra of peptides in 4 vol % TFE-$d_3$ in 90% $H_2O$ 10% $D_2O$ were recorded on a Varian Inova 600 MHz NMR spectrometer at 308 K and pH 5.1 using preirradiation of the water resonance. Typical 90° degree pulses were 9.2 µs for both 1D, NOESY and TOCSY spectra, and the spinlock pulse in the TOCSY experiment was 22 ms with a window function of 30 ms. The mixing times were 200 ms for the NOESY experiments and 80 ms for the TOCSY experiments. 2*256 increments were recorded and the data were processed using linear prediction algorithms.

Peptide Synthesis and Purification.

The peptides were synthesized on an Applied Biosystems automated Pioneer peptide synthesizer using standard Fmoc chemistry. A typical synthesis was performed on a 0.1 mmol scale using a PAL-PEG-PS polymer (Perspective Biosystems), that forms an amide at the C-terminal of the peptide after cleavage. The substitution level of the polymer was 0.17-0.23 mmol/g. The side chains of the amino acids were protected using base stable groups; t-butyl ester (OtBu) for Asp and Glu, tert butoxymethyl (Boc) for Lys and Orn, trityl (Trt) for Asn and Gln and 2,2,4,6,7-pentamethyldihydrobenzofuran-5-sulfonyl (Pbf) for Arg. The Fmoc group was removed from the amino acid by 20% piperidine in NN-dimethylformamide (DMF, peptide synthesis grade). TBTU (O-(7-benzotriazole-1-yl)-1,1,3,3-tetramethyluronium tetrafluoroborat) (0.5M in DMF) was used together with DIPEA (diisopropylethylamine) (1M in DMF) as the activating reagent and a four fold excess of amino acid was used in each coupling. A standard coupling time of 60 minutes was used except for Nle and Leu where 30 minutes was used and for Gln, Arg, Asn and some difficult passes in the sequence where 90 minutes was used. The N-terminal of the peptide was capped with acetic anhydride in DMF (0.3 M). When the synthesis was completed the polymer was rinsed with dichloromethane and dried under vacuum. The peptide was cleaved from the resin and deprotected by treatment with a mixture of TFA:$H_2O$:ethanedithiol:triisopropyl silane (94:2.5:2.5:1 v/v), 10 mL per gram of polymer, for three hours at room temperature. After filtration and concentration, the peptide was precipitated by the addition of cold diethyl ether, centrifuged and resuspended three times in diethyl ether and lyophilized. The crude products were purified by reversed phase HPLC on a semi-preparative C-8 HICHROM column, eluted isocratically with 36-43% isopropanol and 0.1% aqueous TFA at a flow rate of 10 mL/min. The purity was checked by analytical HPLC and the polypeptides were identified by MALDI-TOF mass spectrometry.

The Acylation Reaction.

Stock peptide solutions (1 mM) were prepared by weighing and dissolving the peptide in buffer solution, assuming a water content of the lyophilized peptide of 25%, and adjusting the pH by small additions of NaOH and HCl (1-2 M). A stock substrate solution was also prepared by dissolving p-nitrophenylfumarate in equal volumes of acetonitrile and buffer to the final concentration of 15 mM. The buffers used at pH 5.9 and at pH 8 were Bis-Tris and Tris, respectively. The acylation reaction was carried out by the addition of one equivalent of substrate (2 µl) to the peptide solution (30 µl). At the addition of 1-10 equivalents of 1 to the peptide, 2 µl of substrate solution and 18 µl of buffer were added to 30 µl of the peptide solution (1 mM) in the case of one equivalent. In the case of 10 equivalents 20 µl of substrate solution was added to 30 µl of peptide solution (1 mM) to give a final peptide concentration of 0.6 mM. After three days at room temperature and pH 5.9, or after one day at room temperature and pH 8, the reaction mixtures were analyzed by reversed phase HPLC on an analytical C-8 HICHROM column, eluted isocratically with 36-43% isopropanol and 0.1% aqueous TFA at a flow rate of 0.6 mL/min. The polypeptides were identified by mass spectrometry. The degree of modification was measured by integration of the peaks of the analytical RP HPLC chromatogram, and calculated from the area of each peak divided by the total area of peptide fractions under the assumption that all peptides, modified and unmodified, have the same extinction coefficient.

Trypsin Digestion.

A 1 mM peptide solution in 0.1 M $NH_4^+HCO_3^-$ at pH 8.0 was prepared. One mg of trypsin was dissolved in 100 µL of 0.1 mM HCl and added to the peptide solution which corresponded to 200 g trypsin/mol peptide. After 3 hours at 37° C. the reaction was quenched by the addition of 20 µL HCl and the reaction solution was lyophilized. The resulting fragments were identified by mass spectrometry.

Kinetic Measurements.

The kinetic studies were performed on a Varian CARY 100 Bio UV-Visible or a CARY 5E UV-Vis-NIR Spectrophotometer equipped with a CARY temperature controller at 298 K. A 1 mM peptide stock solution was prepared in buffer and the pH was adjusted to the correct value by the addition of small amounts of 1 M NaOH or HCl. The stock solution was diluted with buffer to the desired concentrations (0.4 mM, 0.3 mM and 0.2 mM) and transferred (270 µl) to the cuvettes. After 15 minutes of temperature equilibration the substrate was added (5 µl, 5 mM) to give a final concentration of 0.1 mM. The p-nitrophenylfumarate was dissolved in a 50% (v/v) mixture of buffer and acetonitrile. The buffers used were sodium acetate (100 mM) at pH 4.1 and 5.1, Bis-Tris (50 mM) at pH 5.85, and pH 7.0, TRIS (50 mM) at pH 8.0 and 9.0 and CAPS at pH 9.7-10.2. The reaction was followed for more than three half-lives and the data was processed using IGOR Pro software. The rate constants are the results from fitting a straight line to the pseudo first order rate constants plotted versus the peptide concentration.

TABLE 1

The mean residue ellipticity at 222 nm/(deg cm² dmol⁻¹).

| Peptide | Mean residue ellipticity $[\theta]_{222}/$ deg cm² dmol⁻¹ | |
|---|---|---|
| | pH 5.9 | pH 8 |
| KA-I | −22200 | −24100 |
| KA-I-Fum | −23600 | — |
| KA-I-A$_{15}$ | −23700 | −25400 |
| KA-I-A$_{33}$ | −22300 | −24800 |
| KA-I-R$_{19}$ | — | −24700 |
| KA-II | −22400 | −21200 |
| KA-II-Fum | −23700 | — |

TABLE 2

The site and estimated degree of mono- and dimodification of peptides at pH 5.9 and pH 8 after reaction with one equivalent of 1. Due to competing background hydrolysis modifications are not complete after reaction with one equivalent of 1. The relative yields, the amounts of mono- or dimodified peptides divided by the total amount of modified peptide, are given within brackets.

| Peptide | Site of modification | Modification | Degree of modification | | | |
|---|---|---|---|---|---|---|
| | | | pH 5.9 | | pH 8 | |
| KA-I | 34 and 19 | mono | 45 | (>90) | 66 | (90) |
| | 34 and 19 | di | <5 | (<10) | 7 | (10) |
| KA-I-A$_{15}$ | 34 and 19 | mono | 36 | (100) | 73 | (94) |
| | 34 and 19 | di | — | — | 5 | (6) |
| KA-I-A$_{33}$ | 34 | mono | 32 | (64) | 45 | (61) |
| | 15 | mono | 13 | (26) | 22 | (30) |
| | 34 and 15 | di | <5 | (<10) | 7 | (9) |

TABLE 2-continued

The site and estimated degree of mono- and dimodification of peptides at pH 5.9 and pH 8 after reaction with one equivalent of 1. Due to competing background hydrolysis modifications are not complete after reaction with one equivalent of 1. The relative yields, the amounts of mono- or dimodified peptides divided by the total amount of modified peptide, are given within brackets.

| Peptide | Site of modification | Modification | Degree of modification | | | |
|---|---|---|---|---|---|---|
| | | | pH 5.9 | | pH 8 | |
| KA-I-R$_{19}$ | 34 | mono | 42 | (>85) | 58 | (85) |
| | 15 | mono | <5 | (<15) | 8 | (12) |
| | 34 and 15 | di | — | — | 2 | (3) |
| KA-II | 12 | mono | 27 | (75) | 57 | (70) |
| | 15 | mono | 9 | (25) | 19 | (23) |
| | 12 and 15 | di | — | — | 5 | (6) |

Multifunctional Folded Polypeptides from Peptide Synthesis and Site-selective Self-functionalization—Practical Scaffolds in Aqueous Solution Results Design of the Helix-loop-helix Dimers.

Sixteen 42-residue peptides have been designed to fold into hairpin helix-loop-helix motifs and dimerize to form four-helix bundles, FIG. 13, Table 3. They were synthesized on an Applied Biosystems Pioneer automated peptide synthesizer, using the Fmoc protection group strategy, purified by reversed-phase HPLC and identified using a Voyager DE-STR MALDI-TOF mass spectrometer from Applied Biosystems. Their designs were based on those of the 42-residue polypeptides SA-42 [S. Olofsson, G. Johanson, L. Baltzer, *J. Chem. Soc., Perkin Trans.* 2 1995, 2047-2056], KO-42 [K. S. Broo, L. Brive, P. Ahlberg, L. Baltzer, *J. Am. Chem. Soc.* 1997, 119, 11362-11372], LA-42b [L. Andersson, G. Stenhagen, L. Baltzer, *J. Org. Chem.* 1998, 63, 1366-1367] that have been described in great detail previously. The sequences were shown previously by NMR and CD spectroscopy and by equilibrium sedimentation ultracentrifugation (SA-42 and KO-42) to fold into hairpin helix-loop-helix motifs that dimerize in an antiparallel way to form four-helix bundles. The polypeptides were designed to form amphiphilic helical segments linked by a short loop, and residues capable of capping, stabilization of the helix dipole moment and formation of salt bridges were introduced to stabilize the folded helices [J. W. Bryson, S. F. Betz, H. S. Lu, D. J. Suich, H. X. Zhou, K. T. O'Neil, W. F. DeGrado, *Science* 1995, 270, 935-941]. In comparison with the sequences of SA-42, KO-42, LA-42b and KA-I six residues or less were changed in the sixteen sequences reported here and there is little reason to suppose that major structural changes occur as a result of these modifications. Nevertheless, the solution structure of one of the polypeptides LA-42h, FIG. 14, was investigated in detail by CD as well as by NMR spectroscopy, whereas the sequences of the remaining fifteen sequences were studied by CD spectroscopy, to probe in a qualitative way that they all folded into the designed motif.

In order to determine in which positions lysines were acylated the most efficiently by His11, the sequences were designed so that the positions of the Lys residues were systematically varied relative to that of the histidine, FIG. 13, Table 3. His mediated acylation of Lys residues was expected to require proximity between His and Lys, and the Lys residues were therefore incorporated in positions that flanked His11, in the same turn of the helix, or in helical turns before or after the turn of His11. To test the hypothesis that His mediated acylation requires spatial proximity lysine residues were also introduced in positions 18 and 19, two turns away from His11, at a distance between the α-carbons of more than 10 A. These modifications were all carried out in helix I, and in positions 7 (i−4), 8 (i−3), 10 (i−1), 14 (i+3), 15 (i, i+4), 18 (i+7) and 19 (i+8). Positions in helix II were also probed although the geometrical relationship is not as clearly defined between His11 and residues of helix II. The inventor and co-workers have previously reported on catalytic sites for ester hydrolysis where cooperative effects between residues in positions 11 and 34 have been observed [K. S. Broo, H. Nilsson, J. Nilsson, A. Flodberg, L. Baltzer, *J. Am. Chem. Soc.* 1998, 120, 4063-4068]. His11 was therefore concluded to be in close proximity to the residue in position 34 and lysines were introduced in positions 30 and 34. The preference for acylation of each lysine residue was determined by measuring the degree and site of acylation of each polypeptide, and by replacing each one of the most reactive lysines in turn by Ala residues, Table 3. As the preferentially acylated lysine was replaced by an Ala or Ser residue the acylation of the second most reactive lysine could be observed, and the hierarchy of reactivities determined.

Sequences designed to probe the role of serine residues in Lys acylation were also designed, where Ser was introduced in positions 8, 15, 19 and 34. The side chain of Ser is an alcohol and the intention of incorporating Ser residues was to determine whether Ser acylation could also be achieved via the His mediated pathway, but no evidence of intermediates or reaction products due to Ser acylation were obtained. However, serine residues were found to affect the site selectivity, as discussed below.

The sequence LA-42h, FIG. 14 and SEQ. ID. No. 7, was designed to provide a scaffold for the introduction of three different substituents in a stepwise reaction without intermediate purification in aqueous solution at room temperature, to demonstrate the usefulness of the folded sequence in synthesizing a complex structure with ease and in high yield. The design was based on the relative reactivities of individual lysine and ornithine residues determined previously, and in the present series of polypeptides. His11 was known to mediate the preferential acylation of Lys15, Orn34 was shown to be the most reactive residue in the direct acylation reaction at pH 8 and since Lys residues in position 8,10 and 14 were found in the present investigation to be of approximately equal reactivity. Lys8 was introduced to carry the third mately equal reactivity. Lys8 was introduced to carry the third substituent because of the spatial proximity between residues 8, 15 and 34.

The Structure of the Folded Helix-Loop-Helix Dimers.

The secondary structure of LA-42h was determined by CD spectroscopy and the spectrum showed the characteristics of an α-helical protein with minima at 208 and 222 nm. The mean residue ellipticity of LA-42 h at 222 nm was −20 100 deg cm² dmol⁻¹ in 100 mM Bis-Tris:Tris buffer at pH 5.9 and room temperature. The mean residue ellipticity of LA-42h showed no pH dependence in the interval from 4 to 9 and it was independent of concentration in the interval from 0.2 mM to 1 mM, FIG. 15.

The secondary and tertiary structures of LA-42h were investigated by ¹H-NMR spectroscopy. The ¹H-NMR spectrum of LA-42h was assigned from the TOCSY and NOESY spectra recorded in H₂O:D₂O (90:10 v/v) containing 4 vol % of TFE-d₃ at 308 K using methods described in detail previously [S. Olofsson, L. Baltzer, *Folding & Design* 1996, 347-356]. Most of the spin systems of the amino acids were identified from the αH—NH region in the TOCSY spectrum and the sequential assignments of residues 5 to 19 and 23 to 41 were obtained from the NH—NH region in the NOESY spectrum. Due to the cis-trans equilibrium of Pro21, an extra set of resonances with low intensity from the amino acids near the proline in the loop region was identified. The αH chemical shifts are diagnostic of secondary structure formation, and the measured values were compared to tabulated values for random coil conformations [D. S. Wishart, B. D. Sykes, F. M. Richards, *J. Mol. Biol.* 1991, 222, 311-333]. From their upfield shifts relative to the random coil values, two helical segments were identified in the sequence of LA-42h from Ala5 to Nle16 and from Ala25 to Arg40. A loop region was also assigned from the downfield shifts, or absence of deviation relative to random coil conformation, of the α protons. Medium-range NOEs typical of α-helix formation, αH—NH i, i+3 and i, i+4, were found in the sequence from Nle5 to Arg19 in helix I and from Ala24 to Ala41 in helix II, see supporting information. The NOE connectivities between the aromatic protons of the phenylalanine side chains of residues 35 and 38, and the methyl protons of Ile9 and Leu12 showed that the peptide folds into a helix-loop-helix motif and the connectivity between aromatic ring protons and the methyl group of Nle16 suggests that it dimerizes in an antiparallel manner to form a four helix bundle.

The secondary structures of the folded peptides other than LA-42h were investigated by CD spectroscopy and the spectra showed the characteristics of α-helical proteins with minima at 208 and 222 nm. The mean residue ellipticities at 222 nm of the peptides were in the range between −17 500 and −28 000 deg cm² dmol⁻¹ at pH 5.9 in 50 mM Bis-Tris buffer, which is well in the range of previously designed helix-loop-helix dimers, see supporting information. The inventor concludes that all polypeptides reported here fold into hairpin helix-loop-helix motifs The acylation of Lysine Residues.

In order to explore the selectivity of lysine acylation the peptides were reacted at approximately 1 mM concentration with one equivalent of the active ester, p-nitrophenyl fumarate (I), at room temperature and pH 5.9. The reaction mixture was analyzed by analytical HPLC and the resulting peaks in the chromatogram were integrated and the peptides were identified as unmodified, monomodified and dimodified by MALDI TOF mass spectrometry. Tryptic digestion of each peptide was used to determine the sites of modification. The tryptic fragments were identified by MALDI-TOF MS and the analysis was based on the known capacity of trypsin for cleaving peptides on the C-terminal side of the positively charged residues lysine and arginine. No cleavage occurs if the side chain of Lys has been modified, and in addition to preventing cleavage, acylation increases the weight of the fragment by the mass of the acyl group. The degrees and sites of modification are shown in Table 3.

The reaction between the peptide and the substrate competes with the spontaneous hydrolysis of the substrate to form the corresponding carboxylic acid and the reaction with one equivalent of I leads to incomplete modification since some of the substrate is hydrolyzed. The fraction of substrate expected to be incorporated can be estimated from the pseudo first-order rate constant of the peptide self-catalyzed reaction and the first-order rate constant of the spontaneous hydrolysis. For preparative purposes compensating amounts of substrate can thus be added to ensure optimal incorporation but in the determination of the degree of modification no compensation was undertaken, as the purpose was to identify the site that was the most reactive in competition with other sites.

LA-42b has a histidine in position 11 (i), lysines in positions 10 (i−1), 15 (i+4), 19 (i+8), 33 (helix II) and an ornithine in position 34 (helix II). It was 60% monoacylated at position 15 after reaction with one equivalent of I, and no other reaction products were observed, Table 3. When the lysine in position 15 was replaced by a serine, in the peptide P1, the new main site of modification was Orn34 and the degree of monomodification was 49%, although minor amounts of peptides acylated at positions 10 and 19 were also identified. Lys15 therefore competes favorably with Orn34 in capturing the acyl group of I. The selectivity is very high since monoacylation at Orn34 was never observed in peptides with His11, Lys15 and Orn34 in the sequence. Orn34 was only acylated in peptides containing a Lys15, when Lys15 had already become acylated. The removal of Lys15 reduced the reactivity of the peptide towards the ester showing that Lys15 enhances the reactivity of His11, probably by depressing the pKa of the His residue through an electrostatic effect and by stabilizing the tetrahedral transition state by the same mechanism. The second order rate constant, Table 4, of the reaction of LA-42b with I was decreased from 0.18 $M^{-1}s^{-1}$ to 0.04 $M^{-1}s^{-1}$ upon replacing Lys15 by a Ser residue. The reduced overall reactivity does not affect the site selectivity of the polypeptides but the competition between spontaneous hydrolysis and functionalization becomes less favorable although it is easily improved by increasing the concentration of peptide and thereby the rate of incorporation. Replacing both Lys15 and Orn34 by Ala residues in P2 led to a peptide with low reactivity that was only acylated at the side chain of Lys10, and only to a low degree. In LA-42b the hierarchy of reactivities was therefore Lys15, Orn34 and Lys10, with very little acylation of other lysines in the sequence. The low reactivity of Lys10 is advantageous because it makes the selectivity high, and because the degree of incorporation can be improved by the addition of excess substrate if functionalization of Lys10, after functionalization of Lys15 and Orn34, is attempted.

The reactivity was increased in the peptide P3 by introducing Lys14, which is known to depress the pKa of His11, and the second-order rate constant was increased from 0.04 to 0.07 $M^{31}\ {}^1s^{-1}$. Again Orn34 was the preferred site of modification, the competition between Lys14 and Orn34 results in approximately ten times more acylation of Orn34 than of Lys14. The degree of incorporation was 4% at Lys 14 and 43% at Orn34. No acylation of Lys10 was observed in P3, suggesting that Lys14 competes favorably with Lys10 for the acyl group at the side chain of His11, but the low degree of modification made direct comparisons difficult. Orn34 was therefore replaced by an Ala residue in the peptide P4, and the degree of acylation determined and found to be equal between Lys10 and Lys14, with a yield of 12% at each side chain. Lys10 and Lys14 are therefore equally reactive. Other positions in the proximity of His11 are 7 and 8, and the introduction of Lys 7 in P5 and Lys8 in P6 led to incorporation in low yields at both positions. The degree of incorporation at Lys7 and Lys8 was approximately 50% higher than at Lys10 which was also present in the sequences, which makes Lys7 and Lys8 sites of comparable reactivity to those of Lys10 and Lys14. In synthesizing a multiply modified protein scaffold Lys7, Lys8, Lys10 and Lys14 are therefore alternative positions for incorporation, depending on the required geometry. The small difference in the degrees of acylation of lysines in positions 7, 8, 10 and 14 suggests that these different positions can be used equally well in combination with Lys15 and Orn34 in the formation of trisubstituted polypeptide scaffolds.

The acylation of Lys or Orn residues in helix II, was investigated by the incorporation of Lys30 to probe whether His mediated acylation could be extended further in the folded motif. Orn34 in helix II was selectively acylated in the absence of Lys15 and the reaction of a peptide that contained a lysine in position 30 as well as in position 10, 19 and 33, but alanines in positions 15 and 34, provided a probe of the reactivity of position 30. Upon reacting the polypeptide P7 with one equivalent of I, Lys30 was 22% monoacylated but 13% of acylation was also observed in position 10 and the intramolecular reactivity of Lys30 was therefore less than a factor two higher than that of Lys10. Nevertheless, the possibility to acylate Lys30 expands the available geometries of incorporation.

To probe whether His mediated acylation could be extended beyond one turn of a helix the peptides P8 and P9 were synthesized where Lys18 was introduced and the competition from Lys15 and Orn34 had been eliminated by replacement by a Ser and an Ala residue, respectively. Only trace amounts of acylation were detected and only at Lys10. Acylation of Lys19 was only observed in trace amounts in the peptides P1, P3, P10 and P11 and possibly due to a direct pathway due to a pKa reduction of the Lys19 residue that enhances its reactivity. The inventor concludes that only residues in close proximity to His11 were acylated via the His-mediated pathway. The substrate is consumed by reaction with the His residue, to form amide bonds or to be hydrolyzed, and by spontaneous hydrolysis. Direct acylation of lysine residues can not in general compete with His mediated reactions at low pH because the nucleophilicity of histidine residues is higher than that of lysines.

Orn acylation has been shown previously to proceed efficiently even when there are no His residues in the proximity, because position 34 is formally in a hydrophobic core position according to the pattern of the heptad repeat. However, at pH 5.9 the degree of incorporation in P1 is higher than what is observed in polypeptides without flanking His residues, and it is likely that Orn34 is acylated both via a His-mediated pathway and via a direct pathway.

The Effect of Ser Residues on the Degree of Acylation.

In order to begin understanding the role of residues not directly involved in bond forming or bond breaking steps, sequences were designed where serine residues were introduced, FIG. 13, Table 3. The sequence P10 was the same as that of P1 except that Ala8 and Ser15 in P1 were changed to Ala15 and Ser8 in P10. As a result the efficiency of the acylation of Orn34 was decreased, the degree of modification of P1 was 49% whereas the degree of modification of P10 was only 38%. Along the same lines the peptide P3 was compared with the peptide P11, where the same residues had been subjected to an identical exchange of positions. Here the effect on the degree of acylation was again to reduce the degree of acylation of Orn34, and to reduce the efficiency and selectivity of the site selective acylation. In the peptide P12 the incorporation of Ser8 and the removal of Ser15, both exchanged for Ala residues, led to a substantial increase in the site selectivity as Lys10 was favored by a factor of two over Lys14 in P12, although the residues were acylated to an equal extent in P4. In the peptide P13 Ser15 and Ser19 were introduced in an attempt to affect the possible acylation of Lys18, but surprisingly the introduction of Ser19 appeared to affect only the acylation of Lys10. In spite of the fact that Lys10 and Lys14 were both present, and had previously been shown to be of equal reactivity, P13 was selectively acylated at Lys10 and in relatively good yield, 25%. In the peptide P14, in comparison with that of P2, Ala34 was replaced by Ser and the degree of acylation of Lys10 was reduced by approximately a factor of two.

The role of the serines is not understood as the modification pattern is affected but the mechanism remains unclear. A possible explanation may be that the serine is involved in hydrogen bonding to the acyl intermediate and that therefore reaction pathways are favored that lead to acylation of specific lysine residues. The serine might also disrupt the structure of the helix and affect the relative positions of residues involved in acyl transfer, although no effects on helical content by the incorporation of serine residues could be detected. No evidence of serine acylated intermediates was obtained, suggesting that covalent catalysis is not involved and Ser incorporation did not lead to alternative sites of acylation, only the site selectivity was affected. The incorporation of residues other than those directly involved in acyl transfer can therefore be expected to have a profound influence on site selectivity and the efficiency of incorporation and expand the usefulness of protein scaffolds.

His-mediated Acyl Transfer Versus Direct Acylation of Lys Residues.

To determine if all of these positions were acylated via the His-Lys pathway a reference peptide, Pref, was designed, Table 3. The histidine was removed and lysines were introduced in positions 8, 10, 14, 19, 30, and 33, Lys15 and Orn34 were both excluded. After reaction with one equivalent of I at room temperature and pH 5.9 the reaction mixture was analyzed by reversed phase HPLC. The five resulting peaks were identified by MALDI-TOF MS to be unmodified peptide (found m/z 4264.4, theoretical m/z 4265.0), monomodified peptide (three peaks)(found m/z 4363.3, theoretical m/z 4363.0) and dimodified peptide (found m/z 4461.3, theoretical m/z 4461.1). Lys19 was the main acylation site with a degree of modification of 41%. The two other sites that were modified to 7% each were Lys8 and Lys30. In the presence of a His residue all esters react with the His side chain, and only Orn34 can compete with the His mediated pathway. Lysines that are not close to His are not acylated and the site selectivity is high. In the absence of a His residue, Lys and Orn residues compete with the spontaneous hydrolysis reaction and even though reaction rates are low, lysines are acylated but with little site selectivity, the exception being Orn34 or other lysines in hydrophobic environments with depressed pKa values.

His mediated acylation transfers were extraordinarily efficient between His11 and Lys15 and of a significantly lower efficiency between His11 and other flanking lysine residues. Orn34 was mainly acylated through a direct mechanism because of the low pKa induced by the hydrophobic character of position 34. The efficiency of the His-mediated pathway is therefore a key factor in four-helix bundle functionalization. The lysine in position i+4 is strongly favored over all other flanking lysines in helix I as well as over the lysine and ornithine residues in helix II whereas more remote lysines in helix I, Lys18, Lys19 and Lys33, were not acylated by His11. Orn34 was the second most efficient site of modification and was acylated by a combination of His mediated and direct acylation pathways. Site-selective incorporation of three different residues into positions 15, 34 and 8 was therefore considered to be optimal for the synthesis of a triple substituted four-helix bundle.

The Site Selective Triple Functionalization of a Folded Four-helix Bundle Protein in Aqueous Solution.

Based on the results presented above LA-42h was designed for the selective incorporation of three different functional groups in a one-pot reaction in aqueous solution. The strategy included the His-Lys mediated pathway that is favored at pH 5.9 and the direct acylation pathway that is the most efficient at pH 8. The sequence of LA-42h was based on that of LA-42b with a histidine in position 11, a lysine in position 15 with the addition of a lysine in position 34, FIG. 14. The third residue to be functionalized, Lys8, was chosen due to its position on the surface of the peptide. It was shown above that the side chains of Lys8 and Lys10 are of comparable reactivity and Lys10 was therefore replaced by an arginine to avoid competing acylation. In LA-42b there is a lysine in position 19, to stabilize the macroscopic dipole of the helix. This lysine was replaced by an arginine since it was shown to compete with Orn34 in KA-I. The strategy was to direct the first functional group via the His-Lys mediated reaction pathway to position 15 at pH 5.9, then raise the pH to 8 and to direct the next group to position 34 via the direct acylation reaction and then again lower the pH to 5.9 and address the final position and introduce the third group. The His-Lys mediated reaction is efficient at pH 5.9 and the intramolecular competition between the lysines in positions 15 and 8 ensures that the first substituent will be incorporated with high selectivity at the side chain of Lys15.

The Stepwise Multifunctionalization Reaction

Three substrates p-nitrophenyl fumarate (I), p-nitrophenyl 3-($\beta$-D-galactopyranosyl-1-thio)propionate (II) [M. Elofsson, B. Walse, J. Kihlberg, *Tetrahedron Letters* 1991, 32, No. 51, 7613-7616; L. K. Andersson, G. T. Dolphin, J. Kihlberg, L. Baltzer, *J. Chem. Soc., Perkin Trans.* 2 2000,459-464] and p-nitrophenyl acetate (III) were chosen to demonstrate the stepwise introduction of three different substrates into a folded helix-loop-helix polypeptide motif. In order to simplify the pH change from 5.9 to 8 a mixture of the two buffers Bis-Tris and Tris were used, each at concentrations of 100 mM. In the first step 1.7 equivalents of I were reacted with LA-42h at pH 5.9 and room temperature. After three days a sample from the reaction mixture was analyzed by analytical HPLC and 67% of monomodification at the side chain of Lys15 was observed. The reaction mixture was also analyzed by MALDI-TOF MS and it was confirmed that the peptide was mainly monomodified, (found m/z 4600.1, theoretical m/z 4600.2), but unmodified peptide remained and a small amount of dimodified peptide was also observed. The pH of the reaction solution was adjusted to 8 and three equivalents of II were added and after 24 hours HPLC analysis showed that 35% had become dimodified. MS analysis of the reaction mixture showed that the main product was peptide modified by I and II (found m/z 4849.8, theoretical m/z 4850.5). The pH was then lowered to 5.9 and 10 equivalents of m were added. HPLC analysis followed by MALDI-TOF analysis showed that 30% of the peptide was trimodified with the three different substituents (found m/z 4891.4, theoretical m/z 4892.5) and the sites of modification were identified by tryptic digestion followed by HPLC ESMS and MALDI-TOF MS to show that the peptide had been modified by I at Lys15, II at Lys34 and III at Lys8, see supporting information.

The incorporation was also performed in the reverse order by starting at pH 8 with modification of Lys34. In the first step 1.5 equivalents of I was added to the peptide at pH 8 and HPLC analysis showed that the peptide had become monomodified to a level of 50%; but 33% of dimodification was also observed. In the second step the pH was lowered to 5.9 and 2.1 equivalents of II were added. HPLC analysis showed that 30% of the peptide was dimodified with I and II. At the same pH, 10 equivalents of III were then added to the reaction mixture and analysis by HPLC showed 28% of trimodified peptide. The modification sites were identified by tryptic digestion of the purified peptide and the resulting fragments were identified by LC-ESMS. The masses found corresponded to the peptide segments, see supporting information, and the identity of the target peptide was unequivocally established.

To demonstrate the general applicability of the protein scaffold a second incorporation with different substituents was carried out with the galactose derivative, II, a cellobiose derivative IV [L. K. Andersson, G. T. Dolphin, J. Kihlberg, L. Baltzer, *J. Chem. Soc., Perkin Trans.* 2 2000, 459-464; M. Elofsson, S. Roy, B. Walse, J. Kihlberg, *Carbohydrate Research* 1993, 246, 89-103] and a high-affinity ligand for the protein human carbonic anhydrase II, the N-hydroxysuccinimide ester of 4-carboxy benzenesulfonamide V [A. E. Eriksson, P. M. Kylsten, T. A. Jones, A. Liljas, *Proteins: Structure, Function, and Genetics* 1988, 4, 283-293]. The example demonstrates the design of a scaffold that can be used to study the effect of glycosylation on the interplay between two proteins driven by a high affinity interaction. However, the number of possible applications to the study of protein-protein interactions, and to the inhibition of such interactions is virtually endless, and a variety of intramolecular competition experiments can be envisioned where ligands of different affinity can compete for the active site of the enzyme.

LA-42h at 1 mM concentration was reacted with 1.7 equivalents of I at pH 5.9, with 1.3 equivalents of V at pH 8, and with 10 equivalents of IV at pH 5.9. HPLC analysis and MS analysis of the reaction product showed that the desired functionalized folded four-helix bundle was obtained in 30% yield, FIG. 16. The reaction is therefore of general applicability.

Discussion

A four-helix bundle protein scaffold ensures water solubility for covalently linked groups, tremendous versatility in design and the opportunity to present a wide variety of functionalities in a large number of well-defined geometries. In spite of these advantages designed proteins have not been used to any great extent as scaffolds in supramolecular chemistry or for purposes of studying biomolecular interactions, most likely because of our poor understanding of how to construct new proteins, the so called protein folding problem. Major advances in protein design have recently led to a number of non-natural sequences that fold according to prediction but in order to exploit these novel scaffolds methods must be available that makes it possible to introduce easily and efficiently new functions by design. While solid phase peptide synthesis methods have been developed to a high level of efficiency and selectivity, the introduction of expensive groups on the solid phase remains a cost inefficient alternative. Derivatives of amino acids that carry non-natural functional groups require non-trivial synthesis efforts and the protected, chiral amino acid must be available in typically 2.5 to 4-fold excess over the growing polymer chain. Orthogonal protection groups have been developed that allow the site selective modification of side chains of the naturally occurring amino acids in an important development of solid phase synthesis schemes, to provide the best alternative in generating molecular diversity during solid-phase synthesis. However, self-catalyzed reactions represent a very easy alternative by allowing the incorporation of very small amounts of substrate in aqueous solution at mild pH and room temperature. Because control of reactivity and selectivity resides in the amino acid sequence, little control over reaction conditions is required by the chemist, and the reaction can be left on the lab bench until complete. The incorporation depends on competition between polypeptide residues and spontaneous hydrolysis, and the competitive situation is relatively insensitive to external disturbances.

With the advent of site selective acylation reactions designed proteins may be functionalized in a large number of ways using very simple chemistry. The inventor and co-workers have previously reported on the mechanisms for site-selective acylation of lysine residues, directly or via a His mediated pathway. The inventor and co-workers have now mapped the site-selectivities of individual lysine residues that flank the nucleophilic histidine, beyond those in positions i,i−3 and i,i+4 in a helical segment reported previously, and determined their relative reactivities. The inventor has also probed the possibility that residues that appear not to participate in the making and breaking of bonds, in this case serine residues, can affect the site selectivities of the functionalization reactions. The mapping of all sites that surround the His residue has provided the understanding of how to multifunctionalize the four-helix bundle in several steps by adding active esters in a stepwise fashion.

The opportunity to address individual lysine residues to incorporate virtually any functional group that can be transformed into an active ester, provides a vehicle for constructing receptors for biomacromolecules and small organic compounds, but also the introduction of functions beyond binding. For example, the incorporation of fluorescent dyes or the attachment to solid supports paves the way for reporting and biosensing. The protein scaffold can be reacted with any functional group that is water soluble and that can be presented in the form of an active ester. The inventor and co-workers have demonstrated the use of sugar derivatives [L. K. Andersson, G. T. Dolphin, J. Kihlberg, L. Baltzer, *J. Chem. Soc., Perkin Trans.* 2 2000, 459-464], enzyme inhibitors, fluorescent probes, acetyl [L. K. Andersson, G. T. Dolphin, J. Kihlberg, L. Baltzer, *J. Chem. Soc., Perkin Trans.* 2 2000, 459-464] and fumaryl [L. Baltzer, A.-C. Lundh, K. Broo, S. Olofsson, P. Ahlberg, *J. Chem. Soc., Perkin Trans.* 2 1996, 1671-1676] groups but obviously peptide esters, DNA, PNA and RNA derivatives, steroids, and small molecule libraries can also be incorporated to provide a large variety of receptors, catalysts and molecular devices. Insoluble groups can be introduced on the solid phase using orthogonal protection group strategies, and when these methodologies are used in combination the number of functionalized proteins that can be produced is limited only by the number of applications.

A critical issue is the structure of the functionalized protein as the designed function may depend upon an unmodified fold upon functionalization. The helix-loop-helix dimer motif folds mainly due to hydrophobic interactions between the non-polar residues of amphiphilic helices, but it is known to dissociate at low concentrations and form unstructured monomers. However, the polypeptide KE-2 which was designed for biosensor applications was shown by CD to remain highly folded even at 1 μM concentration, and furthermore it remained folded even when bound to the target protein, human carbonic anhydrase [K. Enander, L. K. Andersson, G. T. Dolphin, B. Liedberg, I. Lundström, L. Baltzer, *J. Org. Chem.*, 67(9), 3120-3123]. Should the need arise to have access to fully folded motifs at nM concentrations the monomeric subunits can be ligated to form a single chain four-helix bundle using the strategies of chemical ligation, in which case dissociation does not occur.

The sequences reported here do not represent separate scaffolds but a single one, and depending on the application, to ensure optimum selectivity and yields of synthesis, some lysines are introduced while others are replaced by non-reactive residues. Alanines are introduced where a non-reactive site is required and arginines where pKa depressions are of interest and to ensure solubility and a practical overall charge. Therefore the helix-loop-helix scaffold is a very versatile one, that is readily synthesized and functionalized. Applications can be envisioned in the biomedicinal area, in the field of proteomics, in drug development and in functional devices such as biosensors.

Conclusions

The inventor has demonstrated the simple and practical introduction of three different residues site-selectively and without intermediate purification into a folded four-helix bundle polypeptide motif in aqueous solution at pH 5.9 and at pH 8. This is the first demonstration of the site-selective incorporation of three different residues into a folded protein using only the reactivities of the naturally occurring amino acids to control reactivity and selectivity. The simple procedure required to perform the functionalization suggests that it may open the way for the use of designed proteins as scaffolds for the study of biomolecular interactions and for a number of applications. The overall yield of incorporation was shown to be 30% or better, for widely different substituents and the scaffold is therefore expected to be useful for the incorporation of virtually any water soluble ester derivatives.

Experimental Section

Mass Spectrometry.

MALDI-TOF MS analyses were performed on an Applied Biosystems Voyager DE-STR mass spectrometer using α-cyano-4-hydroxycinnamic acid as the matrix. The mass spectrometer was calibrated with calibration mixture 2 that contains angiotensin I, ACTH clip1-17, ACTH clip 18-39, ACTH clip 7-38 and bovine insulin. Measured molecular weights corresponded to calculated ones within 1.1 mass units in all cases, and typically within 0.5 mass units. ES MS analyses were performed on a VG ZabSpec magnetic sector instrument. For LC-ESMS analyses tile peptides were eluted with a MeOH:H$_2$O mixture containing 1% HOAc, using a gradient from 10% to 90% MeOH over 20 minutes on a 5 μ C-18 Kromasil column with a flow rate of 75 μl/min. CsI was used for calibration.

NMR Spectroscopy.

NMR spectra of the peptides were recorded on Varian Inova 600 spectrometer at 308 K, in H$_2$O:D$_2$O (90:10 vol %) with 4 vol % TFE-d$_3$ at pH 5.1. Water suppression was accomplished by using preirradiation of the water resonance. The 90° degree pulses were 7.5 μs for both 1D, NOESY and TOCSY spectra, and the spinlock pulse in the TOCSY experiment was 18.5 μs with a window function of 30 μs. The mixing times were 200 ms for the NOESY experiments and 80 ms for the TOCSY experiments. 2*256 increments were recorded with 32 transients in each increment. The data were processed using linear prediction algorithms.

CD Spectroscopy.

CD spectra were recorded on a Jasco J-715 CD spectropolarimeter, in 0.1, 0.5, or 1 mm cuvettes in the interval from 280-190 nm at room temperature. Each spectrum is an average of six scans and the background was subtracted from the spectrum before the mean residue ellipticity at 222 nm was measured. A 1 mM stock peptide solution was prepared by dissolving the peptide in buffer, under the assumption that the lyophilized peptide contains 25% water. The pH was adjusted by addition of small amounts of 0.1 M-1 M NaOH or HCl. For the concentration dependent studies the stock peptide solution was diluted to the desired concentrations by pipetting. A 0.3 mM stock peptide solution in water was prepared for the pH dependent studies and the pH was adjusted by small additions of HCl or NaOH. The concentration of the stock solution for the concentration dependent measurement was determined by quantitative amino acid analysis. 50 mM Bis-Tris buffer at pH 5.9 was used for all peptides except LA-42h and 100 mM Bis-Tris:Tris (1:1) at pH 5.9 was used for LA-42h.

General Procedure for Peptide Synthesis and Purification.

The polypeptides were synthesized on an Applied Biosystems Pioneer™ automated peptide synthesizer on a 0.1 mmol scale using standard Fmoc chemistry. A PAL-PEG-PS polymer was used with a substitution level of 0.16-0.23 mmol/g. TBTU (O-(7-benzotriazole-1-yl)-1,1,3,3-tetramethyluronium tetrafluoroborat) (0.5M in DMF) and DIPEA (diisopropylethylamine) (1M in DMF) was used together with an excess of four equivalents of amino acid in each coupling. A standard coupling time of 60 minutes was used, except for Nle and Leu where 30 minutes coupling was used and for Gln, Arg and Asn where 90 minute couplings were used. The side chains of the amino acids were protected with base labile groups; t-butyl ester (OtBu) for Asp and Glu, tert butoxymethyl (Boc) for Lys and Orn, trityl (Trt) for Asn and Gln and 2,2,4,6,7-pentamethyldihydrobenzofuran-5-sulfonyl (Pbf) for Arg. The Fmoc group was removed from the amino acid by 20% piperidine in DMF. The N-terminal of the peptide was capped using a 0.3 M solution of acetic anhydride in DMF. After the completed synthesis the resin was rinsed with DAM and dried under vacuum. The peptide was cleaved from the resin to create an amide at the C-terminal and deprotected at room temperature using a mixture of TFA:H$_2$O: Ethanedithiol:Triisopropyl silane (94:2.5:2.5:1 v/v), 10 ml per gram of polymer, for three hours. After filtration and concentration, the peptide was precipitated by addition of cold diethyl ether, centrifuged and resuspended three times in diethyl ether and lyophilized.

The synthesis of LA-42b was performed as described above except that a Gly-PEG-PS polymer was used with a substitution level of 0.17 mmol/g and no capping was performed. This polymer does not create an amide at the C-terminal. The crude products were purified by reversed phase HPLC on a semi-preparative C-8 HICHROM column, eluted isocratically with 36-43% isopropanol and 0.1% TFA in water at a flow rate of 10 ml/min. The purity was checked by analytical HPLC and one symmetric peak was found and identified by mass spectrometry.

General Procedure for Determining the Site Selectivity of the Acylation Reaction.

A 1 mM stock peptide solution was prepared by dissolving the weighed peptide in 50 mM Bis-Tris buffer at pH 5.9, under the assumption that the peptide contains 25% water, and by adjusting the pH with small additions of 1-2 M NaOH and HCl. A 15 mM stock solution was also prepared of the substrate p-nitrophenyl fumarate in Bis-Tris buffer:AcCN (1:1 v/v). One equivalent of substrate was added to the peptide solution and in a typical acylation experiment 2 μl of the substrate solution was added to 30 μl of peptide solution. After three days in room temperature the reaction mixture was analyzed by reversed phase HPLC on an analytical C-8 HICHROM column, eluted isocratically with 38-43% isopropanol and 0.1% TFA in water at a flow rate of 0.6 ml/min. The resulting peaks were identified by mass spectrometry. The degree of modification was estimated from the analytical RP-HPLC chromatogram, as the area of each peak divided by the total area of peptide fractions assuming that all peptides, modified and unmodified, have the same extinction coefficient.

Tryptic Digestion.

A 1 mM peptide solution in 0.1 M $NH_4^+HCO_3^-$ at pH 8.0 was prepared and 0.5 mg of typsin was dissolved in 50 μl 0.1 mM HCl and added to the peptide solution to give a final trypsin concentration of 200 g trypsin/mol peptide. After 3 hours at 37° C. the reaction was quenched by addition of HCl (20 μl) and the reaction solution was lyophilized. The resulting fragments were identified by either MALDI-TOF MS or LC-ESMS.

Kinetic Measurements.

The kinetic studies were performed on a Varian CARY 100 Bio UV-Visible or a CARY 5E UV-Vis-NIR Spectrophotometer equipped with a CARY temperature controller. All measurements were performed at 298 K. A 1 mM peptide stock solution was prepared in 50 mM Bis-Tris buffer at pH 5.9 and the pH was adjusted to the correct value by addition of small amounts of 1M NaOH and HCl. The stock solution was diluted with Bis-Tris buffer to the desired concentrations (0.4 mM, 0.3 mM and 0.2 mM) and 270 μl was transferred to the cuvettes. After 15 minutes of temperature equilibration 5 μl of a 5 mM substrate solution was added to give a final concentration of 0.1 mM. The p-nitrophenyl fumarate was dissolved in Bis-Tris buffer/AcCN (1/1 v/v). The reaction was followed for more than 3 half-lives at 320 nm and the data was then processed using IGOR Pro software. The plotting of the absorbance versus time gives the pseudo first order rate constant $k_{obs}$ and the second order rate constant is obtained by fitting a straight line to the pseudo first order rate constants plotted versus the peptide concentration.

General Procedure for the Incorporation of Three Substituents.

A 1 mM peptide solution was prepared in 100 mM Bis-Tris:Tris buffer (1:1) and the pH was adjusted to 5.9 by small additions of 1-5 M NaOH and HCl. The substrate was dissolved in buffer:AcCN (1:1) to a final concentration of 40 mM and 1.7-3 equivalents were added to the peptide solution. After three days at room temperature a small sample of the reaction mixture was analyzed by analytical RP HPLC and MALDI-TOF MS. The pH was adjusted to 8 by small additions of 1-5 M NaOH and HCl and 1.3-3 equivalents of the second substrate were added. After one day at room temperature the reaction mixture a small sample was analyzed by analytical RP HPLC and MALDI-TOF MS. The pH was adjusted to 5.9 by small additions of 1-5 M NaOH and HCl and 10 equivalents of the final substrate was added and after the reaction was complete the reaction mixture was analyzed by analytical RP HPLC and MALDI-TOF MS. The sites of modification were determined by tryptic digestion followed by MS analysis.

TABLE 3

The amino acid sequences of LA-42b and the derived peptides, which have the same sequence as LA-42b except for in 1 to 6 positions. All lysines and ornithine residues are shown in bold and the positions of monomodification in italic. The degree of monomodification is given inside brackets after the position for modification.

| Peptide | 7 i-4 | 8 i-3 | 10 i-1 | 11 i | 14 i+3 | 15 i+4 | 18 i+7 | 19 i+8 | 30 helix II | 33 helix II | 34 helix II |
|---|---|---|---|---|---|---|---|---|---|---|---|
| LA-42b | A | A | K | H | E | *K* (60) | A | K | Q | K | Orn |
| P1 | A | A | *K*[b] | H | E | S | A | *K*[b] | Q | K | *Orn* (49) |
| P2 | A | A | *K* (11) | H | E | A | A | K | Q | K | A |
| P3[a] | A | A | K | H | *K* (4) | S | A | *K*[b] | Q | K | *Orn* (43) |
| P4[a] | A | A | *K* (12) | H | *K* (12) | S | A | K | Q | K | A |
| P5 | *K* (18) | S | *K* (10) | H | E | A | A | K | Q | K | A |
| P6 | A | *K* (20) | *K* (13) | H | E | A | A | K | Q | K | A |
| P7 | A | A | *K* (13) | H | E | A | A | K | *K* (22) | K | A |
| P8 | A | A | *K*(3) | H | E | S | K | A | Q | K | A |
| P9 | A | A | *K*(5) | H | E | S | K | S | Q | K | A |
| P10[a] | A | S | *K*[b] | H | E | A | A | *K*[b] | Q | K | *Orn* (38) |
| P11[a] | A | S | K | H | *K* (4) | A | A | K | Q | K | *Orn* (34) |
| P12 | A | S | *K* (12) | H | *K* (6) | A | A | K | Q | K | A |
| P13 | A | A | *K* (25) | H | K | S | K | S | Q | K | A |
| P14 | A | A | *K*(6) | H | E | A | A | K | Q | K | S |
| Pref[a] | A | K (7) | K | A | K | A | A | K (41) | K (7) | K | A |

[a] A small amount of dimodification was seen (<6%) the positions for dimodification have not been established.
[b] The marked residues were monomodified to a minor extent (<5% of the total monomodification) estimated from the MS analysis of the tryptic digests. The different positions for monomodification were not separable on analytical HPLC.

TABLE 4

Second order rate constants for reaction of peptides with I at pH 5.9 and 298K.

| Peptide | $k_2/M^{-1}s^{-1}$ |
|---|---|
| LA-42b | 0.18 |
| P1 | 0.04 |
| P3 | 0.07 |
| P10 | 0.04 |
| P11 | 0.07 |

TABLE 5

The mean residue ellipticity at 222 nm, pH 5.9 of LA-42b and related peptides.

| Peptide | $[\theta]_{222}/$ deg cm$^2$ dmol$^{-1}$ |
|---|---|
| LA-42b | −19000 |
| P1 | −17800 |
| P2 | −24500 |
| P3 | −18100 |
| P4 | −27600 |
| P5 | −23400 |
| P6 | −22700 |
| P7 | −23200 |
| P8 | −22700 |
| P9 | −21300 |
| P10 | −17900 |
| P11 | −18700 |
| P12 | −23800 |
| P13 | −18400 |
| P14 | −21900 |
| PRef | −24400 |

TABLE 6

Fragments found after MALDI-TOF MS analysis of the tryptic digest of LA-42h after reaction with I at pH 5.9, II at pH 8 and III at pH 5.9.

| Fragment | m/z Theoretical | m/z Found | Position of Modification | Substituent |
|---|---|---|---|---|
| 1-10 | 1184.1 | 1184.5 | 8 | acetate (III) |
| 11-19 | 1106.2 | 1106.4 | 15 | fumarate (I) |
| 20-33 | 1410.6 | — | — | |
| 34-40 | 1118.3 | 1118.4 | 34 | galactose (II) |

TABLE 7

Fragments found after MALDI-TOF MS analysis of the tryptic digest of LA-42h after reaction with I at pH 8, II at pH 5.9 and III at pH 5.9.

| Fragment | z | m/z Theoretical | m/z Found | Position of Modification | Substituent |
|---|---|---|---|---|---|
| 1-10 | 1 | 1184.1 | 1184.8 | 8 | acetate (III) |
|  | 2 | 529.2 | — | | |
| 11-19 | 1 | 1258.4 | — | 15 | galactose (II) |
|  | 2 | 629.2 | 630.1 | | |
| 20-33 | 1 | 1410.6 | — | — | |
|  | 2 | 705.3 | 706.1 | | |
| 34-40 | 1 | 966.1 | 966.7 | 34 | fumarate (I) |
|  | 2 | 483.0 | 484.0 | 34 | fumarate (I) |

The invention claimed is:

1. A polypeptide consisting of a four helix bundle formed of two dimerized helix-loop-helix motifs, said helix-loop-helix motifs independently of each other having a sequence according to SEQ ID NO: 1, SEQ ID NO: 2, SEQ ID NO: 3, SEQ ID NO: 4, SEQ ID NO: 5 or SEQ ID NO: 7.

2. A polypeptide consisting of a four helix bundle formed of two dimerized helix-loop-helix motifs, one of said helix-loop-helix motifs having a sequence according to SEQ ID NO: 6, and the other of said helix-loop-helix motifs having a sequence according to SEQ ID NO: 1, SEQ ID NO: 2, SEQ ID NO: 3, SEQ ID NO: 4, SEQ ID NO: 5 or SEQ ID NO: 7.

* * * * *

SEQUENCE LISTING

```
<160> NUMBER OF SEQ ID NOS: 8

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence: Synthetic
      KA-1 peptide
<220> FEATURE:
<221> NAME/KEY: MOD_RES
<222> LOCATION: (5)
<223> OTHER INFORMATION: Nle
<220> FEATURE:
<221> NAME/KEY: MOD_RES
<222> LOCATION: (16)
<223> OTHER INFORMATION: Nle
<220> FEATURE:
<221> NAME/KEY: MOD_RES
<222> LOCATION: (27)
<223> OTHER INFORMATION: Nle
<220> FEATURE:
<221> NAME/KEY: MOD_RES
<222> LOCATION: (34)
<223> OTHER INFORMATION: Orn

<400> SEQUENCE: 1

Asn Ala Ala Asp Xaa Glu Ala Ala Ile Lys Ala Leu Ala Glu Lys Xaa
 1               5                   10                  15

Ala Ala Lys Gly Pro Val Asp Ala Ala Gln Xaa Ala Glu Gln Leu Ala
```

```
                20                  25                  30

Lys Xaa Phe Glu Ala Phe Ala Arg Ala Gly
        35                  40

<210> SEQ ID NO 2
<211> LENGTH: 42
<212> TYPE: PRT
<213> ORGANISM: Artificial Sequence
<220> FEATURE:
<223> OTHER INFORMATION: Description of Artificial Sequence: Synthetic
      KA-I-A15 peptide
<220> FEATURE:
<221> NAME/KEY: MOD_RES
<222> LOCATION: (5)
<223> OTHER INFORMATION: Nle
<220> FEATURE:
<221> NAME/KEY: MOD_RES
<222> LOCATION: (16)
<223> OTHER INFORMATION: Nle
<220> FEATURE:
<221> NAME/KEY: MOD_RES
<222> LOCATION: (27)
<223> OTHER INFORMATION: Nle
<220> FEATURE:
<221> NAME/KEY: MOD_RES
<222> LOCATION: (34)
<223> OTHER INFORMATION: Orn

<400> SEQUENCE: 2

Asn Ala Ala Asp Xaa Glu Ala Ala Ile Lys Ala Leu Ala Glu Lys Xaa
 1               5                  10                  15

Ala Ala Lys Gly Pro Val Asp Ala Ala Gln Xaa Ala Glu Gln Leu Ala
            20                  25                  30

Lys Xaa Phe Glu Ala Phe Ala Arg Ala Gly
        35                  40

<210> SEQ ID NO 3
<211> LENGTH: 42
<212> TYPE: PRT
<213> ORGANISM: Artificial Sequence
<220> FEATURE:
<223> OTHER INFORMATION: Description of Artificial Sequence: Synthetic
      KA-I-A33 peptide
<220> FEATURE:
<221> NAME/KEY: MOD_RES
<222> LOCATION: (5)
<223> OTHER INFORMATION: Nle
<220> FEATURE:
<221> NAME/KEY: MOD_RES
<222> LOCATION: (16)
<223> OTHER INFORMATION: Nle
<220> FEATURE:
<221> NAME/KEY: MOD_RES
<222> LOCATION: (27)
<223> OTHER INFORMATION: Nle
<220> FEATURE:
<221> NAME/KEY: MOD_RES
<222> LOCATION: (34)
<223> OTHER INFORMATION: Orn

<400> SEQUENCE: 3

Asn Ala Ala Asp Xaa Glu Ala Ala Ile Lys Ala Leu Ala Glu Lys Xaa
 1               5                  10                  15

Ala Ala Lys Gly Pro Val Asp Ala Ala Gln Xaa Ala Glu Gln Leu Ala
            20                  25                  30

Lys Xaa Phe Glu Ala Phe Ala Arg Ala Gly
        35                  40

<210> SEQ ID NO 4
```

<211> LENGTH: 42
<212> TYPE: PRT
<213> ORGANISM: Artificial Sequence
<220> FEATURE:
<223> OTHER INFORMATION: Description of Artificial Sequence: Synthetic
      KA-I-R19 peptide
<220> FEATURE:
<221> NAME/KEY: MOD_RES
<222> LOCATION: (5)
<223> OTHER INFORMATION: Nle
<220> FEATURE:
<221> NAME/KEY: MOD_RES
<222> LOCATION: (16)
<223> OTHER INFORMATION: Nle
<220> FEATURE:
<221> NAME/KEY: MOD_RES
<222> LOCATION: (27)
<223> OTHER INFORMATION: Nle
<220> FEATURE:
<221> NAME/KEY: MOD_RES
<222> LOCATION: (34)
<223> OTHER INFORMATION: Orn

<400> SEQUENCE: 4

Asn Ala Ala Asp Xaa Glu Ala Ala Ile Lys Ala Leu Ala Glu Lys Xaa
 1               5                  10                  15

Ala Ala Lys Gly Pro Val Asp Ala Ala Gln Xaa Ala Glu Gln Leu Ala
            20                  25                  30

Lys Xaa Phe Glu Ala Phe Ala Arg Ala Gly
        35                  40

<210> SEQ ID NO 5
<211> LENGTH: 42
<212> TYPE: PRT
<213> ORGANISM: Artificial Sequence
<220> FEATURE:
<223> OTHER INFORMATION: Description of Artificial Sequence: Synthetic
      KA-II peptide
<220> FEATURE:
<221> NAME/KEY: MOD_RES
<222> LOCATION: (5)
<223> OTHER INFORMATION: Nle
<220> FEATURE:
<221> NAME/KEY: MOD_RES
<222> LOCATION: (16)
<223> OTHER INFORMATION: Nle
<220> FEATURE:
<221> NAME/KEY: MOD_RES
<222> LOCATION: (27)
<223> OTHER INFORMATION: Nle
<220> FEATURE:
<221> NAME/KEY: MOD_RES
<222> LOCATION: (34)
<223> OTHER INFORMATION: Orn

<400> SEQUENCE: 5

Asn Ala Ala Asp Xaa Glu Ala Ala Ile Lys Ala Leu Ala Glu Lys Xaa
 1               5                  10                  15

Ala Ala Lys Gly Pro Val Asp Ala Ala Gln Xaa Ala Glu Gln Leu Ala
            20                  25                  30

Lys Xaa Phe Glu Ala Phe Ala Arg Ala Gly
        35                  40

<210> SEQ ID NO 6
<211> LENGTH: 42
<212> TYPE: PRT
<213> ORGANISM: Artificial Sequence
<220> FEATURE:
<223> OTHER INFORMATION: Description of Artificial Sequence: Synthetic
      LA-42b peptide
<220> FEATURE:

```
<221> NAME/KEY: MOD_RES
<222> LOCATION: (5)
<223> OTHER INFORMATION: Nle
<220> FEATURE:
<221> NAME/KEY: MOD_RES
<222> LOCATION: (16)
<223> OTHER INFORMATION: Nle
<220> FEATURE:
<221> NAME/KEY: MOD_RES
<222> LOCATION: (27)
<223> OTHER INFORMATION: Nle
<220> FEATURE:
<221> NAME/KEY: MOD_RES
<222> LOCATION: (34)
<223> OTHER INFORMATION: Orn

<400> SEQUENCE: 6

Asn Ala Ala Asp Xaa Glu Ala Ala Ile Lys Ala Leu Ala Glu Lys Xaa
 1               5                  10                  15

Ala Ala Lys Gly Pro Val Asp Ala Ala Gln Xaa Ala Glu Gln Leu Ala
            20                  25                  30

Lys Xaa Phe Glu Ala Phe Ala Arg Ala Gly
        35                  40

<210> SEQ ID NO 7
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Nle
<220> FEATURE:
<221> NAME/KEY: MOD_RES
<222> LOCATION: (16)
<223> OTHER INFORMATION: Nle
<220> FEATURE:
<221> NAME/KEY: MOD_RES
<222> LOCATION: (27)
<223> OTHER INFORMATION: Nle

<400> SEQUENCE: 7

Asn Ala Ala Asp Xaa Glu Ala Lys Ile Arg His Leu Ala Glu Lys Xaa
 1               5                  10                  15

Ala Ala Arg Gly Pro Val Asp Ala Ala Gln Xaa Ala Glu Gln Leu Ala
            20                  25                  30

Lys Lys Phe Glu Ala Phe Ala Arg Ala Gly
        35                  40

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Nle
<220> FEATURE:
<221> NAME/KEY: MOD_RES
<222> LOCATION: (16)
<223> OTHER INFORMATION: Nle

<400> SEQUENCE: 8

Asn Ala Ala Asp Xaa Glu Ala Ala Ile Lys Ala Leu Ala Glu Lys Xaa
```

```
         1               5              10              15
Ala Ala Lys Gly Pro Val Asp Ala Ala
                20              25
```